(12) United States Patent
Sommer-Knudsen

(10) Patent No.: US 9,611,312 B2
(45) Date of Patent: Apr. 4, 2017

(54) PREPARATION AND/OR FORMULATION OF PROTEINS CROSS-LINKED WITH POLYSACCHARIDES

(75) Inventor: Jens Sommer-Knudsen, Gordon (AU)

(73) Assignee: ELASTAGEN PTY. LIMITED, Eveleigh, New South Wales (AU)

( * ) Notice: Subject to any disclaimer, the term of this patent is extended or adjusted under 35 U.S.C. 154(b) by 0 days.

(21) Appl. No.: 13/988,462

(22) PCT Filed: Nov. 22, 2011

(86) PCT No.: PCT/AU2011/001503
§ 371 (c)(1),
(2), (4) Date: Jul. 17, 2013

(87) PCT Pub. No.: WO2012/068619
PCT Pub. Date: May 31, 2012

(65) Prior Publication Data
US 2013/0296528 A1    Nov. 7, 2013

Related U.S. Application Data

(60) Provisional application No. 61/344,940, filed on Nov. 23, 2010.

(51) Int. Cl.
| | | |
|---|---|---|
| A61K 8/64 | (2006.01) |
| A61Q 19/08 | (2006.01) |
| A61L 27/22 | (2006.01) |
| C07K 14/78 | (2006.01) |
| A61L 27/20 | (2006.01) |
| A61L 27/26 | (2006.01) |
| C08B 11/08 | (2006.01) |
| C08B 11/12 | (2006.01) |
| C08B 33/04 | (2006.01) |
| C08B 37/00 | (2006.01) |
| C08B 37/02 | (2006.01) |
| C08B 37/08 | (2006.01) |
| C08H 1/00 | (2006.01) |
| C08H 1/06 | (2006.01) |
| C08L 1/28 | (2006.01) |
| C08L 3/14 | (2006.01) |
| C08L 5/00 | (2006.01) |
| C08L 5/02 | (2006.01) |
| C08L 5/04 | (2006.01) |
| C08L 5/08 | (2006.01) |

(Continued)

(52) U.S. Cl.
CPC ........... *C07K 14/78* (2013.01); *A61K 8/64* (2013.01); *A61L 27/20* (2013.01); *A61L 27/22* (2013.01); *A61L 27/26* (2013.01); *A61Q 19/08* (2013.01); *C08B 11/08* (2013.01); *C08B 11/12* (2013.01); *C08B 33/04* (2013.01); *C08B 37/0009* (2013.01); *C08B 37/0021* (2013.01); *C08B 37/0024* (2013.01); *C08B 37/0033* (2013.01); *C08B 37/0063* (2013.01); *C08B 37/0069* (2013.01); *C08B 37/0072* (2013.01); *C08B 37/0075* (2013.01); *C08B 37/0084* (2013.01); *C08B 37/0096* (2013.01); *C08H 1/00* (2013.01); *C08H 1/06* (2013.01); *C08L 1/28* (2013.01); *C08L 1/284* (2013.01); *C08L 1/286* (2013.01); *C08L 3/14* (2013.01); *C08L 5/00* (2013.01); *C08L 5/02* (2013.01); *C08L 5/04* (2013.01); *C08L 5/08* (2013.01); *C08L 5/10* (2013.01); *C08L 89/00* (2013.01); *C08L 89/06* (2013.01); *A61K 2800/91* (2013.01); *A61L 2400/06* (2013.01); *A61L 2430/34* (2013.01)

(58) Field of Classification Search
None
See application file for complete search history.

(56) References Cited

U.S. PATENT DOCUMENTS

| 5,866,165 A | 2/1999 | Liu et al. |
| 5,972,385 A | 10/1999 | Liu et al. |

(Continued)

FOREIGN PATENT DOCUMENTS

| JP | 2000-514698 | 11/2000 |
| JP | 2001-261704 | 9/2001 |

(Continued)

OTHER PUBLICATIONS

Fry, Ann. Rev. Plant Physiol., 1986, 37, 165-86.*
Everaerts et al., J. of Bimedical Materials research, 2007, part A DOI 10. 1002/jbm.a,1176-83.*
Extended European Search Report and Opinion, dated Aug. 5, 2014 for EP 11842615.4 / 2643029.

(Continued)

*Primary Examiner* — James H Alstrum Acevedo
*Assistant Examiner* — Roy Teller
(74) *Attorney, Agent, or Firm* — Jones Day

(57) ABSTRACT

Therapeutic compositions and/or formulations are provided, comprising: at least one cross-linked protein matrix, wherein the at least one cross-linked protein matrix comprises at least one protein residue and at least one saccharide-containing residue, and methods of producing the same. The cross-linked protein matrix may be derived from cross-linking a full length or substantially full length protein, such as tropoelastin, elastin, albumin, collagen, collagen monomers, immunoglobulins, insulin, and/or derivatives or combinations thereof, with a saccharide containing cross-linking agent, such as a polysaccharide cross-linking agent derived from, for example, hyaluronic acid or a cellulose derivative. The therapeutic compositions may be administered topically or by injection. The present disclosure also provides methods, systems, and/or kits for the preparation and/or formulation of the compositions disclosed herein.

40 Claims, 3 Drawing Sheets

(51) Int. Cl.
    *C08L 5/10*         (2006.01)
    *C08L 89/00*      (2006.01)
    *C08L 89/06*      (2006.01)

(56) References Cited

U.S. PATENT DOCUMENTS

| | | |
|---|---|---|
| 6,682,760 B2 | 1/2004 | Noff et al. |
| 2003/0100739 A1 | 5/2003 | Tsai et al. |
| 2003/0176395 A1 | 9/2003 | Sakai et al. |
| 2007/0053987 A1* | 3/2007 | Bayer ............... A61K 47/4823 424/488 |
| 2009/0068250 A1 | 3/2009 | Gravagna et al. |

FOREIGN PATENT DOCUMENTS

| | | |
|---|---|---|
| JP | 2004-515451 | 5/2004 |
| WO | WO 01/79342 | 10/2001 |
| WO | WO 2008/067655 | 6/2008 |
| WO | WO 2009/048930 | 4/2009 |
| WO | WO 2010/053918 | 5/2010 |

OTHER PUBLICATIONS

Official Action, dated Aug. 18, 2015, for corresponding JP 2013-540175 application (English translation provided).
International Search Report dated Jan. 10, 2012 for PCT/AU2011/001503.

\* cited by examiner

PREPARATION AND/OR FORMULATION OF PROTEINS CROSS-LINKED WITH POLYSACCHARIDES

CROSS REFERENCE TO RELATED APPLICATION

This application is the National Phase application of International Application No. PCT/AU2011/001503, filed 22 Nov. 2011, which designates the United States and was published in English, which claims priority to U.S. Provisional Application: U.S. 61/344,940, filed 23 Nov. 2010. Each of these applications are incorporated herein by reference in its their entirety.

FIELD

The present disclosure relates to and may be applied to the preparation and/or formulation of proteins cross-linked with polysaccharides.

BACKGROUND

Injectable implants are currently used to bulk or augment tissues in medical applications ranging from vocal cord reconstruction, fecal and urinary incontinence, through to aesthetic treatments for wrinkles. Current implants are made from a range of materials including hyaluronic acid, proteins such as collagen, polymers such as polylactic acid and biomaterials such as hydroxyapaptite.

For example, hyaluronic acid ("HA"), sometimes referred to as hyaluronan or hyaluronate, is a naturally occurring mucopolysaccharide found in, for example, synovial fluid, vitreous humor, blood vessel walls and umbilical cord, and in other connective tissues. The polysaccharide consists of alternating N-acetyl-D-glucosamine and D-glucuronic acid residues joined by alternating $\beta$-1-3 glucuronidic and $\beta$-1-4 glucosaminidic bonds. Hyaluronic acid based products are cross-linked using a variety of approaches including, e.g., chemicals such as BDDE and divinylsulfane. The cross-linking hyaluronic acid is then micronized to enable injection (e.g., Restylane® and Juvéderm®). The hyaluronic acid implants produce their effect by bulking tissue and retaining moisture in the implant and are slowly resorbed by the body.

Another example is collagen based implants which have been based on collagen extracted from animal or human tissues, further cross-linked (e.g., glutaraldehyde (Zyplast®) or ribose based cross-links (Evolence®)) homogenised and then suspended in saline ready for implantation. Collagen implants produce their effect by bulking tissue in a similar way to hyaluronic acid products; however, they also allow greater cellular infiltration into the implant and production of nascent collagen material.

Approaches using polymers such as polylactic acid (e.g., Sculptra®) and biomaterials such as hydroxyapatite (e.g., Radiesse®) have been based on producing a suspension of particulate material in an injectable gel, typically a polysaccharide such as hyaluronic acid or carboxymethyl cellulose. Particulate implants produce their effect by inducing a foreign body response to the particles which leads to fibroblast encapsulation of the particles and collagen production—bulking the tissue through further tissue build up.

One problem with the current approaches to tissue bulking agents is that they do not enable the delivery of biomaterials which are based on or incorporate full length proteins or substantially full length proteins. Formulations which are based on or incorporate full length, or substantially full length, protein material, similar to those found naturally in the body, are more likely to retain the levels of biocompatibility and self recognition desirable for many of the intended applications. The process of chemical cross-linking typically leads to substantial intra-molecular cross-links which may disrupt the natural structure of the molecule; the micronization or homogenisation techniques used to enable product injection are not conducive to maintaining a full length, or substantially full length, protein molecular structure. In addition, the chemical cross-linking agents used to cross-link hyaluronic acid and proteins have known toxicity and may cause irritation, inflammation or carry carcinogenic risks.

The present disclosure is directed, in part, to providing injectable formulations of coherent biomaterials which are based on or derived from proteins, and enable the incorporated protein residues to retain their full length, or substantially full length, structure, and also enable the protein residues to be protected from rapid resorption and/or breakdown due to, e.g., proteolysis. In addition, the present disclosure is directed in part to biomaterials based on, and derived from, full length, or substantially full length, proteins which are amenable to needle injection, retain a coherent structure, are sufficiently cross-linked to slow resorption in vivo or combinations thereof. In addition, the present disclosure is directed in part to biomaterials which are substantially devoid of toxic chemical cross-linking agents. The present disclosure also provides, in part, methods, systems and/or kits for the preparation and/or formulation of at least one cross-linked protein matrix, comprising at least one protein residue and at least one biomolecule cross-linking agent residue, wherein at least one protein molecule is cross-linked with at least one biomolecule cross-linking agent to form the cross-linked protein matrix. In addition, the present disclosure also provides, in part, systems and/or kits for the preparation and/or formulation of at least one cross-linked protein matrix, comprising at least one protein residue and at least one polysaccharide residue, wherein protein molecules, such as substantially full length protein molecules or full length protein molecules, are cross-linked with polysaccharide cross-linking agents to form the at least one cross-linked protein matrix. There is a need for the compositions, methods, systems and/or kits disclosed herein.

SUMMARY

In certain embodiments, the injectable composition may be at least one cross-linked protein matrix, wherein the at least one cross-linked protein matrix comprises: i) at least one protein residue; and ii) at least one saccharide-containing cross-linking residue.

In certain embodiments, the injectable composition may be a substantially soluble composition in an aqueous and/or physiological medium. In certain embodiments, the injectable composition may be a substantially soluble, partially soluble or substantially insoluble in an aqueous and/or physiological medium.

In certain embodiments, the injectable composition may comprise at least one saccharide-containing residue derived from at least one saccharide-containing cross-linking molecule that may be substantially bioavailable, substantially bioavailable, substantially biodegradeable, substantially bioabsorbable, and/or substantially bioresorbable. In certain aspects, the at least one saccharide-containing residue may comprise at least one polysaccharide residue, at least one oligosaccharide residue or combinations thereof. In certain aspects, the injectable composition may comprise at least one polysaccharide, wherein the at least one polysaccharide residue comprises a low, medium, and/or high molecular weight polysaccharide residue. In certain aspects, the injectable composition may comprise at least one polysaccharide residue having a molecular weight of between about 500 to about 500,000 Daltons. In certain aspects, the injectable composition may comprise at least one saccharide-containing residue, comprising at least one polysaccharide residue or at least one oligosaccharide residue comprising one or more negatively charged functional groups and/or one or more positively charged functional groups. In certain aspects, the injectable composition may comprise at least one polyanionic polysaccharide residue or at least one polyanionic oligosaccharide residue. In certain aspects, the injectable composition may comprise at least one polysaccharide residue that is derived from or comprises the residue of hyaluronic acid, a cellulose derivative, carboxy cellulose, carboxymethyl cellulose, hydroxymethyl cellulose, hydroxypropyl cellulose, hydroxypropyl methylcellulose, hydroxy-propylcellulose, carboxymethyl amylose, xanthan gum, guar gum, α-glucan, β-glucan, β-1,4-glucan, β-1,3-glucan, alginates, carboxymethyl dextran, a glycosaminoglycan derivative, chondroitin-6-sulfate, dermatin sulfate, heparin, heparin sulfate, or biomaterials such as polylactic acid, polyglycolic acid, poly(lactic-co-glycolic) acid, tricalcium phosphate, 1-hydroxyapatite, and/or the pharmaceutically acceptable salts, derivatives, and/or combinations thereof. In certain aspects, the injectable composition may comprise at least one cross-linked protein matrix comprising at least one saccharide-containing residue in a concentration of between about 0.01% to about 30%.

In certain embodiments, the injectable composition may comprise at least one protein residue that is derived from or comprises the residue of a full-length protein. In certain aspects, the injectable composition may comprise at least one protein residue comprising an amine-bearing side chain residue, comprising at least one lysine residue and/or at least one arginine residue. In certain aspects, the injectable composition may comprise at least one protein residue that is derived from or comprises the residue of tropoelastin, elastin, albumin, collagen, collagen monomers, immunoglobulins, insulin, and/or derivatives or combinations thereof.

In certain embodiments, the injectable composition may comprise at least one cross-linked protein matrix that is extrudable to at least or about 10 cm. In certain embodiments, the injectable composition is extrudable. In certain embodiments, the injectable composition is extrudable to a length of between about 5 cm to about 30 cm. In certain embodiments, the injectable composition may comprise at least one cross-linked protein matrix comprising about or at least about 25 mg/ml of protein residue. In certain embodiments, the injectable composition may comprise at least one cross-linked protein matrix comprising between about 1 mg/ml to about 250 mg/ml of protein residue.

In certain embodiments, the injectable composition may comprise at least one cross-linked protein matrix that is prepared by employing: i) an activating agent and/or coupling agent; and ii) a modifying agent and/or auxiliary coupling agent; to form one or more linkages and/or cross-linkages.

In certain embodiments, the injectable composition may be employed therapeutically, comprising in surgery, aesthetics, tissue bulking, treating incontinence, in dermal replacement products, dermatology, dermatological surgery, eye surgery, rheumatology, pharmacology, and/or in the field of cosmetics.

In certain embodiments, methods of preparing the composition, comprises cross-linking at least one protein molecule with at least one saccharide-containing cross-linking molecule, are disclosed. In certain embodiments, the methods of preparing the composition comprises: i) modifying at least one saccharide-containing molecules to comprise at least one reactive chemical group that is complementary to a reactive chemical group on the at least one protein molecule; ii) combining the modified at least one saccharide-containing molecule with the at least one protein molecule; and iii) forming at least one bond between the at least one protein molecule and the modified at least one saccharide-containing molecule.

In certain embodiments, the methods of preparing the composition, comprises: i) modifying the at least one saccharide-containing molecule to comprise at least one reactive chemical group; ii) combining the modified at least one saccharide-containing molecule with the at least one protein molecule, wherein the at least one protein molecule comprise at least one reactive chemical group complementary to the reactive group on the modified at least one saccharide-containing molecule; and iii) forming at least one covalent bond between the at least one protein molecule and the modified at least one saccharide-containing molecule.

In certain aspects, the modified at least one saccharide-containing molecule may comprise a modified polysaccharide molecule that has been prepared by attaching at least one moiety comprising a reactive linker capable of conjugating to a protein molecule or modified protein molecule during solid phase polysaccharide synthesis. In certain aspects, the at least one moiety may be attached by a covalent bond. Furthermore, the at least one moiety may comprise a spacer group. Furthermore, the spacer group may comprise polymerized ethylene oxide. The spacer group may also be PEG or PEO.

In certain embodiments, the conjugate may be formed with a covalent linkage. Furthermore, in certain embodiments, the covalent linkage may be selected from the group comprising: an amide, an oxime, a hydrazone, a sulfide, an ether, an amine such as a secondary or tertiary amine, an enol ether, a thiol ether, an ester, a triazole and a disulfide. In certain aspects, the covalent linkage may comprise an amide or a hydrazone.

In certain embodiments, the methods disclosed may be, robust, more efficient, cost effective, simple and/or combinations thereof.

In certain embodiments, the cross-linked protein matrix may comprise one or more protein residues or modified protein residues. In certain embodiments, the cross-linked protein matrix may comprise two different protein residues or modified protein residues.

In certain embodiments, the cross-linked protein matrix may comprise one or more polysaccharide residues or modified polysaccharide residues. In certain embodiments, the cross-linked protein matrix may comprise two different polysaccharide residues or modified polysaccharide residues.

In certain embodiments, the cross-linked protein matrix may be an injectable composition.

BRIEF DESCRIPTION OF THE FIGURES

The accompanying drawings facilitate an understanding of the various embodiments of this disclosure. Exemplary embodiments of processes, systems, kits, preparations, methods, purifications, or combinations thereof, will now be described in further detail, by way of example only, with reference to the accompanying figures in which.

DETAILED DESCRIPTION

Figure 1:
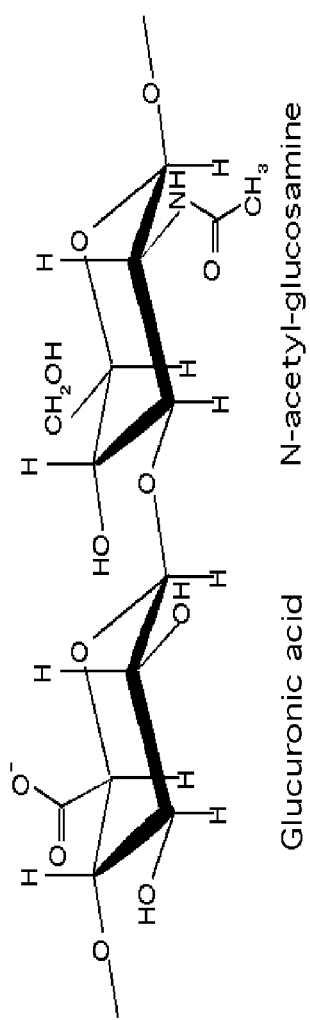
FIG. 1 illustrates, in accordance with certain embodiments, an Ideal Repeating Structure of Hyaluronic Acid. Hyaluronic Acid is a polysaccharide consisting of β-D-glucuronic acid-[1,3]-β-D-N-acetyl-glucosamine disaccharide units, comprising one carboxyl group per disaccharide unit, which may be activated and cross-linked.

The following description is provided in relation to several embodiments which may share common characteristics and features. It is to be understood that one or more features of one embodiment may be combinable with one or more features of the other embodiments. In addition, a single feature or combination of features in certain embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The subject headings used in the detailed description are included only for the ease of reference of the reader and should not be used to limit the subject matter found throughout the disclosure or the claims. The subject headings should not be used in construing the scope of the claims or the claim limitations.

Unless defined otherwise, the technical terms used herein have the same meaning as is commonly understood by one of skill in the art.

The term "activated" may include an intermediate form of a molecule that may be susceptible and/or vulnerable to nucleophilic attack and/or nucleophilic substitution by a nucleophilic compound. For example, in certain embodiments, a carboxyl group containing molecule, such as a saccharide-containing molecule comprising a carboxyl group, for example, a polysaccharide comprising a carboxyl group, may be activated when, for example, it is treated with an activating agent to form an activated intermediate, such as an activated ester, wherein the activated intermediate may be susceptible and/or vulnerable to nucleophilic attack and/or nucleophilic substitution by a nucleophilic compound, such as an amine, to form a linkage between the carboxyl group containing molecule and the nucleophilic compound, such as an amide linkage. In certain embodiments, a hydroxyl containing molecule, such as a saccharide-containing molecule comprising a hydroxyl group, for example, a polysaccharide comprising a hydroxyl group, may be activated when, for example, it is treated with an activating agent to form an activated intermediate, such as an epoxy or halohydrin reactive group, wherein the activated intermediate may be capable of reacting with a compound, such as an amine, to form a linkage between the hydroxyl group containing molecule and the compound, such as a secondary or tertiary amine linkage.

The term "amino acid" may refer to α-amino acids which are racemic, or of either the D- or L-configuration. In certain embodiments, an amino acid may be a naturally occurring amino acid or a non-naturally occurring amino acid, such as a synthetically derived non-naturally occurring amino acid. The designation "d" preceding an amino acid designation (e.g., dAla, dSer, dVal, etc.) refers to the D-isomer of the amino acid. The designation "dl" preceding an amino acid designation (e.g., dlSer) refers to a mixture of the L- and D-isomers of the amino acid.

The term "biocompatible" substance, may include, the ability of a material to perform with an appropriate host response in a specific situation, for example, one that has no medically unacceptable toxic or injurious effects on biological function.

The term "bioconjugate" may refer to a conjugate derived from at least two biomolecules, from at least two biopolymers, or from at least one biomolecule and at least one other biopolymer. The bioconjugate may also include a conjugate derived from three or more biomolecules, biopolymers, and/or combinations thereof, such that at least one of the biomolecules and/or biopolymers is conjugated to more than one biomolecule and/or biopolymer, thereby having intermolecular cross-linkages. The bioconjugate may also include one or more linkages between the individual components that have been conjugated, such as an intramolecular cross-linkage. In certain embodiments, the bioconjugate may have one or more intermolecular cross-linkages, for example, the bioconjugate may be solely intermolecularly cross-linked, or may be substantially or predominantly intermolecularly cross-linked. In certain embodiments, the bioconjugate may have one or more intramolecular cross-linkages, for example, the bioconjugate may be solely intramolecularly cross-linked, or may be substantially or predominantly intramolecularly cross-linked. In certain embodiments, the bioconjugate may have both intermolecular cross-linkages and intramolecular cross-linkages. The bioconjugate may also include one or more spacer groups between the one or more linkages joining the one or more individual components, or the spacer group may be between the individual component and the linkage. For example, the spacer group may include, but is not limited to an ethyleneoxide moiety, a polymer formed from repeating —(—CH$_2$—CH$_2$—O—)— moieties, polyethylene glycol (PEG), polyethylene oxide (PEO), and/or derivatives thereof.

The term "biomolecule" may refer to a compound found in nature, a derivative of a compound found in nature (i.e., a naturally-occurring molecule), a synthetically modified analog of a compound found in nature, a genetically engineered analog of a compound found in nature, or a genetically engineered modified analog of a compound found in nature. For example, a biomolecule may include, but is not limited to, an amino acid, peptide, bio-active peptide, genetically engineered peptide, protein, glycoprotein, bio-active protein, partially digested protein, proteins in its pro-active form, genetically engineered protein, enzyme, antibody, genetically engineered antibody, saccharide, disaccharide, trisaccharide, oligosaccharide, polysaccharide, oligonucleotide, RNA, DNA, peptide nucleic acid (PNA), antigen, oligosaccharide, substrate for an enzyme, substrate for a nuclear receptor, and/or derivatives or combinations thereof.

The term "biopolymer" may refer to a compound found in nature, a derivative of a compound found in nature, a synthetically modified analog of a compound found in nature, a genetically engineered analog of a compound found in nature, a genetically engineered modified analog of a compound found in nature, wherein the biopolymer may be made up of monomeric units. For example, biopolymers may include, but are not limited to, peptides, peptide nucleic acids (PNAs), oligonucleotides, RNA, DNA, proteins, enzymes, antibodies, glycoproteins, trisaccharides, oligosaccharides, polysaccharides, and/or derivatives thereof. In certain embodiments, the biopolymer may be linear or branched, or may be of a particular three-dimensional design, such as a starburst structure, or matrix-like structure. Examples of monomeric units include, but are not limited to, amino acids, amino acid-derivatives, monosaccharides, disaccharides, trisaccharides, sugar-derivatives, PNA monomers, nucleotides, nucleosides, and/or derivatives or combinations thereof.

In certain embodiments, the compounds provided herein may contain chiral centers. Such chiral centers may be of either the (R) or (S) configuration, or may be mixtures thereof. For example, the compounds provided herein may be enantiomerically pure, diastereomerically pure or stereoisomerically pure. In certain embodiments, the compounds provided herein may be stereoisomeric mixtures or diastereomeric mixtures. For example, in the case of amino acid residues, each residue may be of either the L or D form. For example, the preferred configuration for naturally occurring amino acid residues is L.

The term "complementary reactive groups" represents those groups that, when reacted together, form a covalent linkage. For example, an amino reactive group may refer to a moiety that may react directly with amine-reactive containing moiety to form an amide bond or an amine bond. For example, a thiol reactive group may refer to a moiety that may react directly with sulfhydryl-reactive containing group to form a stable sulfide bond. For example, an amino group may be complementary to a carboxyl derivative. For example, an amino group may be complementary to a hydroxyl derivative. For example, a hydrazino group may be complementary to a carbonyl derivative. For example, an oxyamino group may also be complementary to a carbonyl derivative.

The term "conjugate" may represent a compound containing at least two or more components that are linked together, such as at least two or more biomolecules and/or biopolymers that are linked together. The individual components may be linked together directly through one or more covalent bonds, one or more ionic bonds, by chelation, and/or mixtures or combinations of linkages thereof. In certain embodiments, the conjugate may comprise direct linkages between the individual components, such as ionic bonds, or covalent bonds, for example, amide bonds, directly linking the at least two or more biomolecules and/or biopolymers together. For example, the conjugate may comprise a first component, such as a protein, that may be linked directly through one or more covalent bonds to a second component, such as a polysaccharide, to form a conjugate, e.g., a protein-polysaccharide conjugate. In certain embodiments, the conjugate may comprise a spacer group between the individual components, wherein the conjugate comprises at least two linkages via the spacer group to join the two individual components together. For example, a first biomolecule may form a first linkage with a spacer group and a second biomolecule may form a second linkage with the spacer group. The conjugate may include one or more spacer groups between the one or more linkages joining the two or more individual components together, or may be between the individual component and the linkage. For example, the spacer group may include, but is not limited to a glycol moiety, an ethyleneoxide moiety, a polymer formed from repeating —(—CH$_2$—CH$_2$—O—)— moieties, such as polyethylene glycol (PEG), or polyethylene oxide (PEO), a polyamine, a polyol, and/or derivatives or combinations thereof.

The term "cross-linked protein matrix" may refer to one or more protein residues comprising at least one or more cross-linkages to at least one or more molecule residues, such as one or more biomolecule residues and/or one or more biopolymer residues or derivatives or combinations thereof.

The term "residue" may refer to that portion of molecular material or residual molecular material that remains in a reaction product. For example, the portion of protein molecular material that remains in a reaction product, such as a cross-linked product derived from reacting a protein molecule and a cross-linking agent, is called a protein residue. For example, the portion of a saccharide-containing molecular material that remains in a reaction product, such as a cross-linked product derived from reacting a saccharide-containing molecule and a protein molecule, is called a saccharide-containing residue.

The terms "fine needle" or "fine gauge needle" or "fine needle injection" may refer to, but are not limited to, the use of a needle of a size of about 25 G or smaller. Broader gauge needles may also be used in certain applications as discussed further herein.

The term "hyaluronic acid" or "HA" may include hyaluronic acid and any of its hyaluronate salts, including, for example, sodium hyaluronate (the sodium salt), potassium hyaluronate, magnesium hyaluronate, and calcium hyaluronate. Hyaluronic acid from a variety of sources may be used herein. For example, hyaluronic acid may be extracted from animal tissues, harvested as a product of bacterial fermentation, or produced in commercial quantities by bioprocess technology.

The term "linkage" may refer to the connection or bond between two individual molecular components that are linked together. In certain embodiments, the individual molecular components that may be linked together may include, but is not limited to biopolymers, modified biopolymers, such as biologically and/or synthetically modified biopolymers, biomolecules, modified biomolecules, such as biologically and/or synthetically modified biomolecules. For example, the connection or bond between two biomolecules, between a biomolecule and a spacer group, between two biopolymers, between a biopolymer and a spacer group, between two modified molecules, and/or derivatives or combinations thereof. In certain embodiments, the linkage may be stable to thermolysis or hydrolysis or both. In certain embodiments, the linkage may be biocompatible. In certain embodiments, the linkage may be formed by the formation of a covalent bond an ionic bond, and/or combinations thereof. For example, the linkage may be formed by the formation of a combination of one or more covalent bonds and/or one or more ionic bonds. In certain embodiments, the covalent linkage may include, but is not limited to, the formation of an amide bond, an oxime bond, a hydrazone bond, a triazole bond, a sulfide bond, an ether bond, an amine bond such as a secondary or tertiary amine bond, an enol ether bond, an ester bond, a disulfide bond, or mixtures thereof. In certain embodiments, the amide bond may be formed, for example, between a carboxylic acid group or an activated carboxylic acid moiety of a saccharide-containing biomolecule and an amine group of an amino acid-containing biomolecule, such as a protein, for example a protein comprising a lysine residue. For example, in certain embodiments, the amide bond may be between, for example, a biomolecule comprising a modified-saccharide moiety, such as a polysaccharide moiety modified with a spacer group, and a biomolecule comprising an amino acid moiety, such as a protein. In certain embodiments, the amide bond may be between, for example, a biomolecule comprising a saccharide moiety and a biomolecule comprising a modified-amino acid moiety, such as a protein modified with a spacer group.

The term "modified" may refer to a modification of a molecule and/or a moiety on the molecule, such as a biomolecule or a biopolymer, either by naturally occurring processes, synthetic chemical modifications, bio-engineering or the like, and/or combinations or variations thereof. In certain embodiments, the molecule and/or moiety on the molecule may be modified by the transformation of an already existing moiety on the molecule, such as by synthetic chemical transformative processes and/or by naturally occurring processes, the attachment of an additional moiety, and/or combinations or variations thereof. For example, in certain embodiments, the attachment of a moiety onto the molecule may be by the formation of a covalent bond. In certain embodiments, for example, the modified molecule comprising a transformed moiety, may be capable or more capable of reacting with complementary reactive group to form a linkage, cross-linkage, and/or combinations or derivatives thereof. In certain embodiments, for example, the modified molecule comprising an attached moiety, may be capable or more capable of reacting with complementary reactive group to form a linkage, cross-linkage, and/or combinations or derivatives thereof. In certain embodiments, the modified molecule comprising the transformed and/or attached moiety, may include, for example, a reactive group, a linkable group, a spacer group, a complementary reactive group, and/or combinations or derivatives thereof. In certain embodiments, the modified molecule comprising the transformed and/or attached moiety, may comprise a moiety, such as a reactive group, that may be formed and/or deprotected by synthetic chemical modifications or by naturally occurring processes to be available to react to form a linkage or cross-linkage, for example, by reacting with a complementary reactive group. For example, in certain embodiments, the modified molecule may be derived by activating a chemical group, such as a carboxyl group, by attaching a spacer group, by deprotecting a reactive moiety, and/or combinations or variations thereof.

The terms "mole" or "molar concentration (M)" of polysaccharides, as used herein, refer to the moles of the repeating monomeric unit contained within the polymer.

The term "polysaccharide" may include, for example, a saccharide-containing molecule comprising at least three saccharide residues, for example, at least three saccharide monomer repeat units, such as at least three monosaccharide repeat units, at least three disaccharide repeat units, at least three trisaccharide repeat units, at least three oligosaccharide repeat units, and/or combinations or derivatives thereof. In certain embodiments, a polysaccharide may comprise same and/or different saccharide residues, for example, one or more of the same and/or different saccharide residues, two or more of the same and/or different saccharide residues, three or more of the same and/or different saccharide residues, and/or combinations or derivatives thereof.

The term "saccharide-containing molecule" may include, for example, a molecule comprising a monosaccharide, a disaccharide, a trisaccharide, an oligosaccharide, and/or a polysaccharide. In certain embodiments, for example, the saccharide-containing molecule may comprise a monomer repeat unit comprising a monosaccharide, a disaccharide, a trisaccharide, a oligosaccharide, or a polysaccharide. In certain embodiments, the saccharide-containing molecule may comprise one or more of the same or different saccharide monomer repeat units, for example, the saccharide-containing molecule may comprise one or more of the same or different disaccharide, trisaccharide, oligosaccharide, and/or polysaccharide monomer repeat units.

In certain embodiments, the saccharide-containing residue may be derived from an oligosaccharide, modified-oligosaccharide, polysaccharide, modified-polysaccharide, and/or derivatives thereof, or may be derived from a saccharide-containing cross-linking molecule, for example, an oligosaccharide cross-linker, modified-oligosaccharide cross-linker, polysaccharide cross-linker, modified-polysaccharide cross-linker, and/or derivatives thereof.

The term "protein" or "protein unit" or "protein monomer" may include, for example, a full length protein, a substantially full length protein, a protein fragment, a bioactive protein, a bioactive protein fragment, a protein in proactive form, an inactive protein, a protein comprising an active site, a protein comprising a binding site, a protein comprising a proteolytic cleavage site, a partially digested protein, a partially hydrolyzed protein, a protein comprising one or more single-point mutations, a protein comprising about 50 to about 99.99% of full length protein, a protein comprising the conservation of about 50% to about 99.99% of the amino acids in a full length protein. In certain embodiments, the protein may include, for example, a peptide comprising at least one bioactive peptide sequence, a peptide comprising at least one receptor binding site, a peptide comprising at least one proteolytic cleavage site, an oligopeptide, a polypeptide, and/or combinations or derivatives thereof.

In certain embodiments, the protein may include, for example, a protein comprising at least one lysine residue, at least one arginine residue, at least one cysteine residue, at least one serine residue, at least one threonine residue, at least one tyrosine residue, at least one glutamate residue, at least one aspartate residue, at least one proline residue, and/or combinations or derivatives thereof. In certain embodiments, the protein may include, for example, a protein comprising at least one dimeric residue, such as at least one cystine residue.

In certain embodiments, the protein may include, for example, a protein comprising at least one amine group, a protein comprising at least one amine-bearing side chain, a protein comprising at least one amine-bearing amino acid residue, such as a protein comprising at least one lysine residue, a protein comprising at least one arginine residue, and/or combinations or derivatives thereof. For example, in certain embodiments, the protein may include a protein comprising an amine-rich region, such as a lysine-rich region or an arginine-rich region, and/or combinations or derivatives thereof. In certain embodiments, the protein may include, for example, a poly(amine-residue) protein, such as a polylysine, polyarginine, and/or combinations or derivatives thereof.

In certain embodiments, a protein may include homopolymers or copolymers, for example, homopolymers or copolymers of amino acid residues. For example, in certain embodiments, the protein may comprise a homopolymer or copolymer of lysine residues, arginine residues, and/or histidine residues, such as a protein comprising a lysine-rich region. In certain embodiments, for example, the protein comprising a lysine-rich region may comprise at least two lysine units, such as comprising a polylysine region, for example, comprising at least 5 lysine units. In certain embodiments, for example, the protein comprising a arginine-rich region may comprise at least two arginine units, such as comprising a polyarginine region, for example, comprising at least 5 arginine units. In certain embodiments, the may comprise at least two different residue-rich regions, for example, a protein comprising at least one lysine-rich region and at least one arginine-rich region, and/or combinations or derivatives thereof. In certain embodiments, the protein may include, but is not limited to, tropoelastin, elastin, albumin, collagen, collagen monomers, immunoglobulins, insulin, and/or derivatives or combinations thereof.

In certain embodiments, a protein may include a modified protein or protein derivative. In certain embodiments, for example, a modified protein or protein derivative may be a protein prepared from and/or derived from or by naturally occurring processes, synthetic chemical modification, and/or combinations thereof. In certain embodiments, for example, a modified protein or protein derivative may be a protein prepared from and/or derived from or by naturally occurring processes, such as those that occur in eukaryotic cells, prokaryotic cells, and/or combinations thereof. For example, in certain embodiments, naturally occurring processes may include, protein synthesis, protein degradation, hydrolysis, enzymatic processing and/or conjugation, oxidation, reduction, glycosylation, amination, carboxylation, incorporation of an amino acid residue or spacer group (sometimes called a linker group), modification and/or derivatization of an amino acid residue or spacer group, and/or combinations or variations thereof. In certain embodiments, for example, a modified protein or protein derivative may be a protein prepared from and/or derived from or by synthetic chemical modification. For example, in certain embodiments, synthetic chemical modification may include, oxidation, reduction, conjugation, hydrolysis, amination, esterification, amidation, reductive amination, carboxyl group activation, carboxyl group modification, incorporation of an amino acid residue or spacer group (sometimes called a linker group), modification and/or derivatization of an amino acid residue or spacer group, and/or combinations thereof. In certain embodiments, the modified protein or protein derivative may be prepared by solid phase synthesis, solution phase synthesis, and/or combinations thereof. In certain embodiments, a modified protein or protein derivative may be prepared from a protein comprising an amine-bearing amino acid residue rich region, such as a lysine rich region.

In certain embodiments, the protein residue may be derived from a protein and/or derivatives thereof as disclosed herein.

The term "spacer group" may include, for example, a moiety that joins one or more individual components, such as joining a protein and a polysaccharide.

The term "synthetic molecule" may refer to a small molecule or a polymer that is not naturally derived. For example, a synthetic molecule be prepared by chemical modification via solid phase synthesis, solution phase synthesis, or combinations thereof.

Certain embodiments provide methods for modifying or derivatising a saccharide-containing molecule, such as a polysaccharide, with a chemical group that is capable of forming a covalent bond when combined with a protein. The polysaccharide may be modified in a way which enables it to remain soluble, or sufficiently soluble, in water and/or saline solution. The majority of the remaining reactants following the modification of the polysaccharide is removed through, e.g., precipitation or filtration. The modified saccharide-containing molecule, such as a polysaccharide, may then be used as the cross-linking agent. A solution of the modified polysaccharide may then be mixed with the required protein or proteins and allowed to react. The modified chemical groups on the modified polysaccharide react with the protein to form the biomaterials. Biomaterials produced in this way have some unique properties when compared with biomaterials produced using conventional approaches. For example, formulations produced from proteins cross-linked using chemicals which cause intra-molecular cross-links typically are opaque and often coloured white with tints of yellow or brown. Formulations obtained with certain disclosed methods are transparent colourless formulations. Furthermore, proteins cross-linked with chemicals, e.g., glutaraldehyde, may have residual chemical remaining in the formulation which may cause inflammation in vivo and/or reduce the biocompatibility of the product. Formulations obtained with certain disclosed methods are substantially devoid of any such residual chemicals.

Formulations produced utilising chemical cross-linkers or short cross-linking molecules often lead to biomaterials which need to be micronized or homogenised to enable their delivery using syringes or needles; or, require the level of cross-linking to be kept to a minimal level to enable needle extrusion. Proteins cross-linked with chemicals, e.g., glutaraldehyde, that are too heavily cross-linked cannot be extruded through fine gauge needles.

Formulations made by certain disclosed methods can be extruded through fine gauge needles without further processing, or substantial further processing. Certain disclosed formulations retain sufficient cohesiveness even after needle extrusion such that sufficiently long strings of material can be extruded from the needle without the material breaking (e.g. >10 cm, >12 cm, >15 cm, >18 cm, >20 cm, etc.). Furthermore, using certain embodiments described herein, formulations based on full length proteins and using a modified polysaccharide as the cross-linking agent produce a flexible matrix structure which is cable of producing quite firm biomaterials that still retain sufficient flexibility to allow ejection through fine gauge needles.

Cross-Linked Protein Matrix

The cross-linked protein matrix may vary in the disclosed embodiments.

For example, the cross-linked protein matrix may be derived from the cross-linking of one or more protein molecules, such as one or more full length proteins, with one or more saccharide-containing molecules, such as one or more modified saccharide-containing molecules.

For example, the cross-linked protein matrix may include, one or more protein residues that are cross-linked with one or more saccharide-containing residues, such as a saccharide cross-linked protein, a disaccharide cross-linked protein, a trisaccharide cross-linked protein, an oligosaccharide cross-linked protein, or a polysaccharide cross-linked protein.

The cross-linked protein matrix may include, for example, one or more linkages between one or more protein residues via one or more linkages to one or more polysaccharide residues, for example, one or more protein residues may be connected or linked together via one or more linkages to one or more saccharide-containing residues. The cross-linked protein matrix may include, for example, at least one protein residue linked to at least one saccharide-containing residue, such as an oligosaccharide residue or a polysaccharide residue, by one or more covalent bonds and/or one or more ionic bonds or combinations thereof.

The cross-linked protein matrix may include, for example, linkages, i.e., one or more cross-linkages, for example, one or more intermolecular cross-linkages and/or one or more intramolecular cross-linkages or mixtures or combinations thereof. The cross-linked protein matrix may be intermolecularly cross-linked, substantially intermolecularly cross-linked, intramolecularly cross-linked, substantially intramolecularly cross-linked, and/or be both intermolecularly and intramolecularly cross-linked. The cross-linked protein matrix may be derived from one or more cross-linkers, such as a saccharide-containing cross-linker, for example, a polysaccharide or modified polysaccharide, such as hyaluronic acid or modified hyaluronic acid. For example, the cross-linked protein matrix may be derived from one or more cross-linkers, and the one or more cross-linkers may link and/or cross-link to one or more protein molecules and/or form one or more linkages to the same protein molecule. For example, the cross-linked protein matrix may comprise a matrix structure, for example, a matrix of protein residues linked and/or cross-linked, to one or more saccharide-containing cross-linker residues. The matrix structure of a cross-linked protein matrix may provide flexibility, wherein the degree of cross-linking within the cross-linked protein matrix may alter the provided flexibility.

In certain embodiments, the use of a cross-linked protein matrix derived from a full length protein substantially devoid of intramolecular cross-links as disclosed herein may result in a formulation that is more tissue compatible, enhances tissue in-growth, enhances tissue re-growth, or combinations thereof. Such a formulation may also be remodeled into more typical and desirable structures and/or incorporated into the new tissue.

In certain embodiments, the use of a cross-linked protein matrix derived from a substantially full length protein substantially devoid of intramolecular cross-links as disclosed herein may result in a formulation that is more tissue compatible, enhances tissue in-growth, re-growth, or combinations thereof. Such a formulation may also be remodeled into more typical and desirable structures and/or incorporated into the new tissue.

Other embodiments disclosed herein may have a certain degree of intramolecular cross-linking in the protein residue of the cross-linked protein matrix and still provide sufficient properties as to be acceptable for use.

In certain embodiments, the use of a cross-linked protein matrix derived from a substantially full length protein wherein the structure of the protein residue is not substantially masked by the cross-linking process may result in a formulation that is more tissue compatible, enhances tissue in-growth, re-growth, or combinations thereof. Such a formulation may also be remodeled into more typical and desirable structures and/or incorporated into the new tissue.

Degree of Cross-Linking

In certain embodiments, the solubility of the saccharide-containing cross-linking agent, such as a polysaccharide cross-linking agent, may be maintained by using a particular ratio of chemical reagents utilized during the modification, derivatisation, and/or the handling of the polysaccharide. In certain embodiments, to ensure the derivatized polysaccharide does not cross-link with itself, it may require that certain precautions be utilized during the post derivatisation process. For example, the derivatised HA may need to be processed reasonably quickly after it is precipitated in order to wash out the remaining reactants. In certain embodiments, the precipitation of the derivatised HA, the washing off the reactants, and the re-suspending in a water solution may be carried out in approximately 30 minutes. Other time periods may be used depending on the particular situation. For example, the precipitation of the derivatised HA, the washing off the reactants, and the re-suspending in a water solution may be carried out in at least 20, 30 40, 50 minutes, 1 hour, or 2 hours.

In certain embodiments, it may also be useful to further divide the derivatised HA precipitate into smaller pieces prior to dissolution in order to increase the speed of dissolution which may take several hours, for example, at least 1, 2, or 3 hours. Once dissolved it may be desirable, in certain applications, to utilize the derivatised polysaccharide within a certain period of time, for example, within at least 1, 2, 3, 4 or 24 hours. However, this may not be necessary and will depend on the particular formulation and/or application.

In certain embodiments, the protein molecule utilized to form the cross-linked protein matrix in the formulation may be limited by the requirement for appropriate reactive groups to enable it to be cross-linked by the polysaccharide cross-linking agent.

In certain embodiments, at least or about 50% of the protein monomer may be cross-linked with a biomolecule and/or biopolymer, such as a saccharide-containing molecule, for example, an oligosaccharide, polysaccharide, or derivatives thereof. In other embodiments, at least or about 40%, 50%, 60%, 70%, 90%, 95%, 98% or 99% of the protein monomer may be cross-linked with a biomolecule and/or biopolymer or derivatives thereof. In certain embodiments, the protein monomer may be substantially or completely cross-linked with a biomolecule and/or biopolymer.

In certain embodiments, the number of cross-links per possible cross-linking sites per polysaccharide may be at least 0.5%, 1%, 5%, 10%, 15%, 20%, 25%, 30%, 35% or 50%.

In certain embodiments, the number of protein units or protein monomers not incorporated into the cross-linked protein matrix or complex and left unbound may be at least 1, 3, 5, 7, 9, 10%, 15% or 20%. It is desirable in certain applications to minimize the percentage of protein units left unbound after formation of the cross-linked protein matrix or complex. For example, in certain applications it may be desirable to have less than 20%, 15%, 10%, 7%, 5%, 3%, or 1% of the protein units unbound in the formulation after cross-linking. The lack of unbound protein units or protein monomers is one of the benefits of certain applications of the present disclosure.

The percentages may depend on a number of considerations, including but not limited to, the protein selected and the chemistry type selected for the particular application. For example, for tropoelastin and lysine bonds the potential number of sites in some applications is typically around 30 to around 35, so the ratio could be from 1-35 (or around 3% to 100%). With respect to this combination, the preferred percentages for the cross-linked protein matrix may be at least 10%, 20%, 30%, 40%, 50%, 60%, 70%, 80%, 90%, 95% or 99% of the potential number of sites on the one or more protein molecules are cross-linked with one or more biomolecules and/or biopolymers, such as a saccharide-containing molecules, or derivatives thereof.

Another consideration is the length of the saccharide containing molecule, such as polysaccharide, and the chemistry being used for the activation, derivatization, or modification. For example, in certain applications 1 to 30%, 1 to 40%, 3 to 30%, or 5 to 30% of the one or more carboxylic acid groups on a carboxyl group on the oligosaccharide or polysaccharide may be activated with an activating agent, such as NHS to form 1 to 30%, 1 to 40%, 3 to 30%, or 5 to 30% activated esters sites that are available for cross-linking with the protein. For example, in certain applications 1 to 30%, 1 to 50%, 3 to 30%, or 5 to 30% of the one or more hydroxyl groups on the oligosaccharide or polysaccharide may be activated with an activating agent, such as allylglycidyl ether and further modified with a halide, such as bromine, to form 1 to 30%, 1 to 40%, 3 to 30%, 5 to 30% or 1 to 50% activated epoxy or halohydrin sites that are available for cross-linking with the protein. Other chemistries may also be used that are more or less efficient. Another consideration is keeping the percentage of the protein units that may be left as a monomer (i.e., unbound) low, for example, 5% or less.

In certain embodiments, the protein monomer may be cross-linked with a biomolecule and/or biopolymer such that between about 40% to about 99% of the protein monomer may be incorporated into the formulation. In other embodiments, the protein monomer may be cross-linked such that between about 30% to about 99%, about 40% to about 99%, about 50% to about 100%, about 60% to about 100%, about 70% to about 99%, 80% to about 100%, or about 90% to about 100% of the protein monomer may be incorporated into the formulation.

In certain embodiments, the cross-linked protein matrix may have acceptable resistance to biodegradation, degradation, thermolysis, hydrolysis, and/or combinations thereof over a period of time. In certain embodiments, a formulation comprising a cross-linked protein matrix may have acceptable resistance to biodegradation, degradation, thermolysis, hydrolysis, and/or combinations thereof over a period of time. Depending on the cross-linked protein matrix that period of time may be at least 1, 2, 3, 6, 9 or 12 months. Depending on the formulation comprising a cross-linked protein matrix that period of time may be at least 1, 2, 3, 6, 9 or 12 months.

In certain embodiments, a formulation comprising a cross-linked protein matrix may remain acceptably intact and/or persist for from 1 week to 1 year in vivo. Depending on the particular formulation the period of time may vary. For example, the formulation comprising a cross-linked protein matrix may persist for at least 1 to 4 weeks, 2-8 weeks, 1-3 months, 1-6 months, 3-9 months or 6-12 months, 1 week to 24 months, or 12 months to 24 months. In certain embodiments, the formulation comprising a cross-linked protein matrix may persist in vivo for at least 1 week, 2 weeks, 4 weeks, 2 months, 3 months, 6 months, 9 months, 12 months, 15 months, or 24 months.

For example, in certain embodiments, a formulation comprising a cross-linked protein, such as a 0.05 ml, 0.1 ml, 0.2 ml, or 0.5 ml, 1 ml, 2 ml or 3 ml implant, may persist for about 1 week to about 2 years in vivo.

In certain embodiments, the cross-linked protein matrix component within a formulation may be stable to thermolysis, resistant to thermolysis, stable to hydrolysis, resistant to hydrolysis, or combinations thereof during storage of the formulation. For example, the formulation may be stable for at least 6, 12 or 24 months in storage at a temperature of about 2-8° C. The cross-linked protein matrix component within a formulation may be stable to thermolysis, resistant to thermolysis, stable to hydrolysis, resistant to hydrolysis, or combinations thereof during storage of the formulation, if lyophilized and stored at an appropriate temperature, for example, less then or at about −10° C., then it may be stable for several years. The cross-linked protein matrix component within a formulation may be stable to and/or resistant to thermolysis and/or hydrolysis during storage of the formulation at room temperature for at least 1, 2, 3, 4 weeks, 1, 2, 6, or 12 months. In certain embodiments, the cross-linked protein matrix component within a formulation may be stable to and/or resistant to thermolysis and/or hydrolysis during storage at room temperature for between at least 1 week to 12 months, 2 weeks to 8 months, 1 week to 5 weeks, or 1 month to 6 months.

Homologous and Heterologous Cross-Linked Protein Matrixes

The cross-linked protein matrix may vary in structure and composition. The cross-linked protein matrix may include, for example, a cross-linked protein matrix comprising one or more homogeneous or homologous protein residues cross-linked with one or more homogeneous or homologous biomolecules, such as homologous biopolymers. For example, homologous saccharide-containing molecules. A cross-linked protein matrix may comprise one or more homologous protein residues cross-linked with one or more heterogeneous or heterologous biomolecule residues, for example, two or more different biomolecule residues, such as heterologous biopolymer residues. For example, heterologous saccharide-containing residues. A protein cross-linked with one or more different molecules or, two or more different molecules, for example, different biomolecules or biopolymers and/or derivatives or combinations thereof. The cross-linked protein matrix may comprise one or more protein residues cross-linked with one or more different saccharide-containing residues, such as one or more different oligosaccharide or polysaccharide residues, and/or combinations thereof. The cross-linked protein matrix may comprise one or more protein residues cross-linked with a mixture of one or more different polysaccharide residues, such as a blend or mixture of hyaluronic acid residues and carboxymethyl cellulose residues. The cross-linked protein matrix may be prepared from cross-linking one or more protein molecules with a mixture of one or more different activated polysaccharides, such as a blend or mixture of activated-hyaluronic acid and activated-carboxymethyl cellulose.

The cross-linked protein matrix may include, for example, a cross-linked protein matrix comprising a heterologous protein residue, for example, two or more different protein residues, cross-linked with homologous biomolecule residues, such as homologous biopolymer residues, for example, homologous saccharide-containing molecule residues. The cross-linked protein matrix may include, for example, a cross-linked protein matrix comprising a heterologous protein residue, for example, two or more different protein residues, cross-linked with a heterologous biomolecule residue, for example, two or more different biomolecule residues, such as heterologous biopolymer residues, for example, heterologous saccharide-containing residues. The cross-linked protein matrix may comprise one or more different protein residues, for example, two or more different protein residues, cross-linked with a molecule residue, for example, a biomolecule residue, a biopolymer residue, and/or derivatives or combinations thereof. The cross-linked protein may comprise one or more different protein residues, for example, two or more different protein residues, cross-linked with a saccharide-containing residue, such as an oligosaccharide or a polysaccharide residue.

The cross-linked protein matrix may comprise one or more different protein residues, for example, two or more different protein residues, cross-linked with one or more different molecule residues, for example, one or more different biomolecule residues, one or more different biopolymer residues, and/or derivatives or combinations thereof.

For example, the cross-linked protein matrix may comprise one or more different protein residues, for example, two or more different protein residues, cross-linked with one or more different saccharide-containing residues, for example, one or more different oligosaccharide residues and/or one or more different polysaccharide residues, such as two or more different oligosaccharide residues and/or two or more different polysaccharide residues, or mixtures or combinations thereof.

The cross-linked protein matrix may comprise a protein residue cross-linked with one or more different molecule residues, for example, one or more different biomolecule residues, one or more different biopolymer residues, and/or derivatives or combinations thereof. For example, in certain embodiments, the cross-linked protein matrix may comprise a protein residue cross-linked with one or more different saccharide-containing residues, for example, two or more different saccharide-containing residues, for example one or more different oligosaccharide residues and/or one or more different polysaccharide residues, such as two or more different oligosaccharide residues and/or two or more different polysaccharide residues, or mixtures or combinations thereof.

The cross-linked protein matrix may include, for example, one or more protein residues per residue of polysaccharide, such as two or more protein residues per residue of polysaccharide. The cross-linked protein matrix may include, for example, one or more polysaccharide residues per residue of protein, such as two or more polysaccharide residues per residue of protein. In certain embodiments, the cross-linked protein matrix may include, for example, a ratio of about 0.1%-1.5% polysaccharide residue to about 2.5%-10% protein residue. Other examples of ratios are: 0.75%-1.5% polysaccharide residue to 3%-6% protein residue; 0.1%-1.5% polysaccharide residue to 0.1%-6% protein residue; 0.25%-0.85% polysaccharide residue to 1%-4% protein residue; 0.1%-3% polysaccharide residue to 0.5%-15% protein residue; less than or equal to 3% polysaccharide residue to at least 0.5% protein residue; at least 0.25% polysaccharide residue to less than or equal to 15% protein residue; at least 0.01% polysaccharide residue to less than or equal to 12% protein residue; or at least 1% polysaccharide residue to less than or equal to 8% protein residue. Other ratios may be used and will depend on the desired properties and the structure of the protein molecule used to derive the cross-linked protein matrix. For example, in softer formulations the amount of polysaccharide molecule used may be reduced. For example, in certain formulations using longer chain saccharides may permit the use of a lower amount of polysaccharide molecule and still produce acceptable formulations.

In certain embodiments, the cross-linked protein matrix may comprise a biocompatible and/or bioavailable material. For example, the cross-linked protein matrix may be and/or be derived from a biocompatible and/or bioavailable material; or the cross-linked protein matrix may be biocompatible and/or bioavailable.

In certain embodiments, the cross-linked protein matrix may comprise and/or be derived from a water-soluble cross-linker, for example, a water-soluble saccharide-containing cross-linker or a water-soluble modified saccharide-containing cross-linker, such as a water-soluble oligosaccharide cross-linker or a water-soluble modified-oligosaccharide cross-linker. The cross-linked protein matrix may also comprise and/or be derived from a water-soluble polysaccharide-containing cross-linker or a water-soluble modified polysaccharide-containing cross-linker.

In certain embodiments, the cross-linked protein matrix may include, for example, a biomolecule-protein conjugate or a biopolymer-protein conjugate or combinations thereof. For example, the cross-linked protein matrix may include a saccharide-containing molecule-protein conjugate, such as a saccharide-protein conjugate, a disaccharide-protein conjugate, a trisaccharide-protein conjugate, an oligosaccharide-protein conjugate, a polysaccharide-protein conjugate, and/or combinations thereof.

Saccharide-Containing Molecule

In certain embodiments, the saccharide-containing molecule, such as an oligosaccharide, may comprise one or more disaccharides, one or more trisaccharides, two or more disaccharides, two or more trisaccharides, three or more disaccharides, three or more trisaccharides, and/or combinations or derivatives thereof. For example, an oligosaccharide may comprise at least or about 3, 4, 5, 6, 7, 8, or 11 saccharide residues or units. An oligosaccharide used to derive the cross-linked protein matrix, in certain formulations, may also comprise between about 3 to about 15, 3 to about 14, about 3 to about 12, about 3 to about 11, about 3 to about 10, about 4 to about 15, about 5 to about 15, or about 5 to about 10 saccharide residues or units.

In certain embodiments, the polysaccharide, may comprise one or more disaccharide units or residues, one or more trisaccharide units or residues, one or more oligosaccharides; two or more disaccharide units or residues, two or more trisaccharide units or residues, two or more oligosaccharides; three or more disaccharide units or residues, three or more trisaccharide units or residues, three or more oligosaccharides, or combinations thereof. For example, a polysaccharide may comprise at least or about 25, 50, 100, 200, 500, 800, 1,000, 1,200, 1,500, 2,000, 5,000, 10,000, or 20,000, saccharide units or residues. A polysaccharide used to derive the cross-linked protein matrix, in certain formulations, may also comprise between about 25 to about 5000, 500 to about 2000, about 3000 to about 5000, about 150 to about 250, about 175 to about 225, about 100 to about 175, about 150 to about 200, or about 100 to about 200 saccharide residues or units.

In certain embodiments, HA may be used in the range of about 100 to 300 saccharide units or residues, for example around 200 saccharide units or residues. In other embodiments, HA may be used in the range of 200 to 20,000 saccharide units or residues. In other embodiments, HA may be used in the range of about 500 to 2000 saccharide units or residues. In other embodiments, HA may be used in the range of 3000 to 5000 saccharide units or residues. In other formulations, the HA used may comprise at least or about 25, 50, 75, 100, 125, 150, 175 200, 500, 800, 1,000, 1,200, 1,500, 2,000, 5,000, 10,000, or 20,000, saccharide units or residues. The HA used to derive the cross-linked protein matrix, in certain formulations, may also comprise between about 25 to about 5000, 500 to about 2000, about 3000 to about 5000, about 150 to about 250, about 175 to about 225, about 100 to about 175, about 150 to about 200, or about 100 to about 200 saccharide residues or units.

The saccharide-containing molecule, such as a polysaccharide, may be of low, medium, or high molecular weight. For example, the composition or formulation may be derived from a low, medium, or high molecular weight polysaccharide or polysaccharide cross-linking agent.

The low molecular weight saccharide-containing molecule may comprise a molecular weight of between about 25,000 to about 300,000 Daltons, for example, between about 50,000 to about 275,000 Daltons, about 100,000 to about 250,000 Daltons, or about 50,000 to about 300,000

Daltons. The medium molecular weight saccharide-containing molecule may comprise a molecular weight of between about 300,000 to about 900,000 Daltons, about 600,000 to about 800,000, about 500,000 to about 900,000, or about 500,000 to about 750,000 Daltons. The high molecular weight saccharide-containing molecule may comprise a molecular weight of between about 900,000 to about 4,000,000 Daltons, about 1,000,000 to about 3,500,000, about 900,000 to about 3,500,000, about 1,500,000 to about 3,700,000, or about 1,250,000 to about 3,000,000 Daltons. It is also contemplated that polysaccharides may be used that have molecular weight ranges that combine the ranges given herein. For example, a polysaccharide may be used that has a molecular weight range of about 25,000 to about 750,000, about 50,000 to about 900,000, about 100,000 to about 750,000, or about 250,000 to about 500,000 Daltons. Other ranges may also be selected.

In certain embodiments, the ability to use low molecular weight to medium molecular weight polysaccharides makes these approaches easier from a manufacturing/processing perspective. For example, use of lower molecular weight HA allows the HA to be modified, precipitated and washed and the HA remains a reasonably low viscous solution that may be readily used as the cross-linking agent. Using higher molecular weight polysaccharides may provide additional handling issues (e.g., viscous solution, problems with mixing, aeration etc) but, in certain embodiments, a wide range of molecular weights may be used to achieve the desired results. One approach to handling higher molecular weight polysaccharides may be to use a more dilute solution. For example, (e.g., use 1,500,000 Daltons HA but use 0.1% solution to keep viscosity down).

The cross-linked protein matrix may comprise the saccharide-containing residue, such as a polysaccharide residue, in a concentration of between about 0.1% to about 15%. In certain embodiments, the cross-linked protein matrix may comprise the saccharide-containing residue in a concentration of between about 0.1% to about 10%, about 0.2% to about 5%, about 0.25% to about 5%, about 0.1% to about 3.5%, about 0.20% to about 3%, about 0.25% to about 3%, about 0.5% to about 4%, about 0.5% to about 3%, about 0.75% to about 3.5%, about 1% to about 3%, about 1.5% to about 3.5%, or about 0.2% to about 4%.

The saccharide-containing molecule, such as a polysaccharide, may comprise a molecular weight of at least or about 500 Daltons, for example, a molecular weight of at least or about 5,000, 10,000, 25,000, 50,000, 100,000, 150,000, 200,000, 250,000, 300,000, 500,000, 750,000 or 1,500,000 Daltons.

In certain embodiments, a molecule, such as a biomolecule or a biopolymer, may comprise, at least one linkable moiety, such as at least one cross-linkable moiety, for example, a carboxyl group, a hydroxyl group, an amine, a thiol, an alcohol, an alkene, an alkyne, a cyano group, or an azide, and/or modifications, derivatives, or combinations thereof. For example, in certain embodiments, a biomolecule or a biopolymer, such as a protein or a saccharide-containing molecule, for example, an oligosaccharide or a polysaccharide, may comprise, at least one cross-linkable moiety, such as a carboxyl group, a hydroxyl group, an amine, a thiol, an alcohol, an alkene, an alkyne, a cyano group, or an azide, and/or modifications, derivatives, or combinations thereof.

In certain embodiments, a linkable moiety, such as a cross-linkable moiety, may be a moiety that is capable of activation, for example, a carboxyl group moiety or a hydroxyl group moiety, such that activation of the linkable moiety allows and/or facilitates a reaction with a complementary reactive group on the same and/or a second molecule to form a linkage, such as a covalent bond, with the same and/or second molecule, for example, form a cross-linkage to a second molecule, such as a second biomolecule or biopolymer.

In certain embodiments, a molecule, such as a biomolecule or a biopolymer, for example, a saccharide-containing molecule or a protein, may comprise, a spacer group, such that the spacer group is capable of linking to the same and/or a second molecule, for example, a second biomolecule or biopolymer. For example, in certain embodiments, a spacer group may comprise at least one or more linkable moieties thereby enabling the spacer group of linking to the same and/or a second molecule. In certain embodiments, for example, a molecule, such as a saccharide-containing molecule or a protein, may comprise, a spacer group comprising at least one or more linkable moieties, thereby enabling the molecule to form a linkage, such as a cross-linkage, to a second molecule, such as a second biomolecule or biopolymer, for example, a protein or a saccharide-containing molecule, via a linkage formed by the linkable moiety on the spacer group. For example, in certain embodiments, the saccharide-containing molecule, such as an oligosaccharide, polysaccharide, or modified-polysaccharide, may comprise a spacer group comprising at least one or more linkable moieties, such as a carboxyl group or an activated or modified carboxyl group, thereby enabling the polysaccharide to form a linkage, such as a cross-linkage, to a second molecule, such as a protein, for example, a protein comprising an amine, via an amide linkage formed by the linkable moiety on the spacer group on the oligosaccharide, polysaccharide, or modified-polysaccharide.

In certain embodiments, the saccharide-containing molecule, such as an oligosaccharide or a polysaccharide, may comprise negatively charged functional groups or positively charged functional groups, for example, an oligosaccharide comprising negatively charged functional groups or positively charged functional groups; or a polysaccharide comprising negatively charged functional groups or positively charged functional groups; and/or derivatives or combinations thereof. For example, in certain embodiments, the saccharide-containing molecule, such as an oligosaccharide or a polysaccharide, may comprise an iduronic acid, glucuronic acid, or an N-acetylglucosamine residue. In certain embodiments, for example, the saccharide-containing molecule may include, for example, an oligosaccharide comprising a carboxyl group or a polysaccharide comprising a carboxyl group, such as a poly-carboxylic acid containing-polysaccharide, for example, hyaluronic acid or carboxymethyl cellulose; an oligosaccharide comprising an amine group or a polysaccharide comprising an amine group; and/or derivatives thereof.

Structural Features—Linear or Branched

In certain embodiments, the saccharide-containing molecule may include, linear oligosaccharides, branched oligosaccharides, linear polysaccharides, and/or branched polysaccharides. The saccharide-containing molecule may include, but is not limited to, oligosaccharides and/or polysaccharides, such as hyaluronic acid ("HA"); a cellulose derivative, for example, carboxy cellulose, carboxymethyl cellulose, hydroxymethyl cellulose, hydroxypropyl cellulose ("HPC"), hydroxypropyl methylcellulose ("HPMC"), hydroxy-propylcellulosecarboxymethyl amylose ("CMA"); xanthan gum; guar gum; α-glucan; β-glucan; β-1,4-glucan; β-1,3-glucan; alginates; carboxymethyl dextran; a glycosaminoglycan derivative; chondroitin-6-sulfate; dermatin sulfate; heparin; heparin sulfate; polylactic acid ("PLA"); or biomaterials such as polyglycolic acid ("PGA"); poly(lactic-co-glycolic) acid ("PLGA"); tricalcium phosphate ("TCP"); 1-hydroxyapatite ("PAH"); and/or their pharmaceutically acceptable salts or derivatives or combinations thereof. The saccharide-containing molecule may include, a pectin and/or a derivative thereof, including linear and branched oligosaccharides and/or polysaccharides.

The saccharide-containing molecule may be a saccharide-containing molecule prepared from and/or derived from or by naturally occurring processes, synthetic chemical modification, and/or combinations thereof.

For example, the saccharide-containing molecule may include saccharide-containing molecules prepared and/or derived from eukaryotic cells or prokaryotic cells, for example, naturally occurring processes that take place via eukaryotic cells or prokaryotic cells, or combinations thereof.

For example, the saccharide-containing molecule may include saccharide-containing molecules prepared and/or derived by synthetic chemical modification, such as by solid phase synthesis. The saccharide-containing molecule incorporate a linker during solid phase polysaccharide synthesis.

The saccharide-containing molecule may comprise a substantially soluble saccharide-containing molecule, for example, completely soluble, partially soluble, such as an oligosaccharide or polysaccharide that is substantially soluble in an aqueous solution and/or physiological solution.

The saccharide-containing molecule may comprise, for example, a polyanionic saccharide, a polycationic saccharide, a biocompatible saccharide molecule, a bioavailable saccharide, a biodegradeable saccharide, a bioabsorbable saccharide, a bioresorbable saccharide, or combinations thereof.

Protein and Polysaccharide

In certain embodiments, the cross-linked protein matrix may include, for example, a saccharide-containing residue component having an electronic charged character that complements the electronic charged character of the protein residue component in the cross-linked protein matrix. The charge-complementing character of each component may aid and/or facilitate bringing the components together. The charge-complementing character of each component may add to the overall general properties of the composition. The cross-linked protein matrix may further include pharmaceutically and/or physiologically acceptable counter-ions that may complement a saccharide-containing residue component having an electronic charged character, or pharmaceutically and/or physiologically acceptable counter-ions that may complement an electronic charged character of the protein residue component, or both. For example, the cross-linked protein matrix may comprise a polyanionic saccharide-containing residue component, such as polyanionic polysaccharide residue cross-linked to a positively charged protein residue. For example, the cross-linked protein matrix may comprise a polycationic saccharide-containing residue component, such as polycationic polysaccharide residue cross-linked to a negatively charged protein residue.

Choice of Protein and Polysaccharide

In certain embodiments, the choice of the protein component included in the cross-linked protein matrix, such as tropoelastin, may be based on the end functional requirements of the resulting biomaterial product. For example, the protein residue component included in the cross-linked protein matrix may include protein residues such as albumin or collagen residues. In embodiments, the choice of the protein residue component included in the cross-linked protein matrix may be based on the end bioactivity requirement of the resulting biomaterial product. In certain embodiments, the choice of the protein residue component included in the cross-linked protein matrix may be based on the desire to include a combination of protein residues in the resulting biomaterial product.

In certain embodiments, the protein residue component included in the cross-linked protein matrix formulation may vary in the formulation. For example, in certain embodiments, the formulation may have from 25-50 mg/ml of protein residue and 1-30 mg/ml of the polysaccharide cross-linking agent residue. In certain formulations, the protein residue component included in the cross-linked protein matrix formulation may be from 1-200 mg/ml; 5-30 mg/ml, 20-100 mg/ml, 50-200 mg/ml, 20-100 mg/ml, 25-80 mg/ml, 30-60 mg/ml. 40-70 mg/ml, or 25-65 mg/ml. In certain embodiments, the suitable range of amounts of the protein residue component and the suitable range of amounts of the polysaccharide residue component included in the cross-linked protein matrix formulation may be different based on the requirements of the particular application.

Coupling/Conjugating/Cross-Linking

In certain embodiments, the cross-linked protein matrix may be prepared by linking, such as coupling and/or cross-linking, a protein, such as an amine-containing protein, to a saccharide-containing molecule comprising a carboxyl group, a hydroxyl group, an activated carboxyl group, an activated hydroxyl group, a modified carboxyl group or a modified hydroxyl group, such as an oligosaccharide, polysaccharide, and/or derivative thereof, comprising a carboxyl group, a hydroxyl group, an activated carboxyl group, an activated hydroxyl group, a modified carboxyl group or a modified hydroxyl group, to form an amide or amine linkage. For example, the cross-linked protein matrix may be prepared by coupling and/or cross-linking a protein, such as an amine residue bearing protein, to an oligosaccharide and/or modified oligosaccharide comprising a carboxyl group, a hydroxyl group, an activated carboxyl group, an activated hydroxyl group, a modified carboxyl group or a modified hydroxyl group, to form an amide or amine linkage between the protein and the oligosaccharide. For example, the cross-linked protein matrix may be prepared by coupling and/or cross-linking a protein, such as an amine residue bearing protein, to a polysaccharide and/or modified polysaccharide comprising a carboxyl group, a hydroxyl group, an activated carboxyl group, an activated hydroxyl group, a modified carboxyl group or a modified hydroxyl group, to form an amide or an amine linkage between the protein and the polysaccharide.

In certain embodiments, the formation of a cross-linked protein matrix may be facilitated by either the employing of an activating agent and/or coupling agent or the employing of both an activating agent and/or coupling agent and a modifying agent and/or auxiliary coupling agent to form a linkage and/or cross-linkage between the protein component of the cross-linked protein and second molecule of the cross-linked protein, such as a biomolecule, biopolymer, or a spacer group, or combinations or derivatives thereof. The cross-linked protein matrix may be prepared by employing an activating agent and/or coupling agent to form a linkage and/or cross-linkage. For example, the cross-linked protein matrix may be prepared by activating one or more carboxylic acid groups on a carboxyl group containing oligosaccharide or polysaccharide, such as hyaluronic acid, with an activating and/or coupling agent to form an activated-oligosaccharide or activated-polysaccharide, and coupling and/or cross-linking the activated-oligosaccharide or activated-polysaccharide to a protein, such as an amine residue bearing protein, to form an amide linkage between the oligosaccharide or polysaccharide and the protein. For example, the cross-linked protein matrix may be prepared by activating one or more hydroxyl groups on a hydroxyl group containing oligosaccharide or polysaccharide, such as hyaluronic acid, with an activating and/or coupling agent to form an activated-oligosaccharide or activated-polysaccharide, and coupling and/or cross-linking the activated-oligosaccharide or activated-polysaccharide to a protein, such as an amine residue bearing protein, to form an amine linkage between the oligosaccharide or polysaccharide and the protein.

Activating Agent/Coupling Agent/Modifying Agent

In certain embodiments, an activating agent, sometimes called a coupling agent, may include, but is not limited to, a diimide, such as a carbodiimide or a water soluble carbodiimide, for example, 1-ethyl-3-(3-dimethylaminopropyl)-carbodiimide ("EDC"), 1-ethyl-3-(3-dimethylaminopropyl)-carbodiimidemethiodide ("ETC"), 1-cyclohexyl-3-(2-morpholinoethyl)-carbodiimide ("CMC"), and/or the corresponding salts or mixtures thereof. The activating agent may also include, for example, benzotriazole-1-yloxytris-(dimethylamino)-phosphoniumhexafluorophosphate ("Bop-reagent"), O-benzotriazole-1-yl-N,N,N',N'-tetramethlyluronium hexafluorophosphate, bromo-tris-(dimethylamino)-phosphoniumhexafluorophosphate, and/or the corresponding halide salts or mixtures thereof. In certain embodiments, an activating agent, sometimes called a coupling agent, may include, but is not limited to, an epoxide such as allylglycidyl ether or a haloalkene such as allylchloride, and/or the corresponding salts or mixtures thereof.

The cross-linked protein matrix may be prepared by employing both an activating agent and/or coupling agent and a modifying agent and/or auxiliary coupling agent to form a linkage and/or cross-linkage. For example, the cross-linked protein matrix may be prepared by activating one or more carboxylic acid groups on a carboxyl group containing oligosaccharide or polysaccharide, such as hyaluronic acid, with an activating and/or coupling agent to form an activated-oligosaccharide or activated-polysaccharide, modifying the one or more activated carboxylic groups on the activated-oligosaccharide or activated-polysaccharide with a modifying agent and/or auxiliary coupling agent to form a modified-oligosaccharide or modified-polysaccharide, and coupling and/or cross-linking the modified-oligosaccharide or modified-polysaccharide to a protein, such as an amine residue bearing protein, to form an amide linkage between the oligosaccharide or polysaccharide and the protein.

In certain embodiments, a modifying agent, sometimes called an auxiliary coupling agent, may include, but is not limited to, a reagent which, in the presence of an activated carboxyl and/or hydroxyl moiety, such as an activated carboxyl and/or hydroxyl moiety on a polysaccharide, reacts with the activated carboxyl and/or hydroxyl moiety to form a modified species that may be more stable or more capable of reacting with a nucleophile. For example, the modifying agent, or auxiliary coupling agent, may include, but is not limited to, N-hydroxy-succinimide ("NHS"), N-hydroxysulfosuccinimide ("sulf-NHS"), 1-hydroxy-benzotriazole hydrate ("HOBt"), 1-hydroxybenzotriazole monohydrate, 3,4-dihydro-3-hydroxy-4-oxo-1,2,3-benzotriazole (HOOBt), 1-hydroxy-7-azabenzotriazole (HAT), 4-nitrophenol, 2-nitrophenol, 4-nitrothiophenol, 2-nitrothiophenol, pentachlorophenol, pentafluorophenol, imidazole, tetrazole, 4-dimethylaminopyridine, a halide and/or other related compounds.

In certain embodiments, the cross-linked protein matrix may be prepared by activating and/or modifying a saccharide-containing molecule comprising one or more carboxyl and/or hydroxyl groups, such as an oligosaccharide or a polysaccharide, for example, hyaluronic acid, with an activating agent and/or a modifying agent, and combining with a protein, to form one or more linkages and/or cross-linkages, such as one or more amide or amine linkages, between the saccharide-containing molecule and the protein.

The method of preparing a cross-linked protein matrix may comprise mixing and/or combining an activating agent and/or modifying agent with a saccharide-containing molecule comprising one or more carboxyl and/or hydroxyl groups, for example, hyaluronic acid, to form an activated and/or modified saccharide-containing molecule, and mixing and/or combining the activated and/or modified saccharide-containing molecule with a protein, to form one or more linkages and/or cross-linkages, such one or more amide or amine linkages, between the saccharide-containing molecule and the protein. For example, a saccharide-containing molecule comprising one or more carboxyl and/or hydroxyl groups, such as hyaluronic acid, may be activated and/or modified with an activating agent, such as EDC or allylglycidyl ether, and/or modifying agent, such as NHS, HOBt or Bromine. For example, the activated and/or modified saccharide-containing molecule may comprise one or more carboxyl and/or hydroxyl groups activated and/or modified as activated and/or modified esters, such as activated and/or modified triazole esters or as activated and/or modified N-hydroxysuccinimide esters, activated and/or modified epoxides, or activated and/or modified halohydrins. A saccharide-containing molecule comprising one or more carboxyl and/or hydroxyl groups, such as hyaluronic acid, may be activated and/or modified with an activating agent, such as EDC or allylglycidyl ether, and/or modifying agent, such as NHS, HOBt or Bromine, and may be combined, mixed, and/or reacted with a compound bearing one or more amine moieties, such as a protein comprising one or more amine-bearing side chains, to form one or more linkages and/or cross-linkages, such as amide or amine linkages, between the saccharide-containing molecule and the compound bearing one or more amine moieties.

In certain embodiments, a molecule comprising one or more amines moieties, such as a protein, peptide, or spacer group, comprising one or more amines moieties, may be coupled to one or more carboxyl and or hydroxyl groups on a saccharide-containing molecule, for example, may be coupled in an aqueous environment to an oligosaccharide or polysaccharide comprising one or more carboxyl and/or hydroxyl groups, such as an oligosaccharide or polysaccharide comprising one or more carboxyl and/or hydroxyl groups that have been activated and/or modified with an activating agent and/or modifying agent.

In certain embodiments, the method used to modify a polysaccharide may depend on the protein that is cross linked and/or on the polysaccharide used as the cross-linker. For example, the method used to modify a polysaccharide may comprise the use of periodate oxidation. The method used to modify a polysaccharide may comprise the use of an activating agent, such as a carbodiimide, for example EDC. The method used to modify a polysaccharide may comprise the use of an activating agent, such as an epoxide, for example allylglycidyl ether. The method used to modify a polysaccharide may further comprise the use of a modifying agent, such as N-hydroxysuccinimide (NHS) or a halide such as Bromine. For example, hyaluronic acid and/or carboxymethyl cellulose may be activated by an activating agent, such as a carbodiimide, and may be further modified by a modifying agent, such as N-hydroxysuccinimide. For example, hyaluronic acid and/or carboxymethyl cellulose may be activated by an activating agent, such as an epoxide, and may be further modified by a modifying agent, such as Bromine.

Bifunctional Molecular Reagent

In certain embodiments, the cross-linked protein matrix may be prepared by reacting a protein with a multifunctional reagent, such as a saccharide-containing molecule comprising two or more reactive moieties or a spacer group comprising two or more reactive moieties, to form two or more linkages or cross-linkages. For example, the multifunctional reagent may comprise two or more of the same or different reactive moieties, such as a mixture of carboxyl and/or hydroxyl groups, activated carboxyl and/or hydroxyl groups, modified carboxyl and/or hydroxyl groups, and/or combinations or derivatives thereof. For example, each of the reactive moieties on the multifunctional reagent may be reactive with complementary reactive groups on the same or another molecule. For example, one or more of the reactive moieties on the multifunctional reagent may require deprotection, such as removal of a protecting group, to be capable of reacting with the complementary reactive groups on the same or another molecule.

Spacer Group

The spacer group may include a moiety that joins one or more individual components. The spacer group may be linked one or more molecules, for example, linked to a protein by a covalent bond, linked to a polysaccharide by a covalent, linked to both a protein and a polysaccharide by covalent bonds, and/or combinations thereof. The spacer group may include, for example, but is not limited to a glycol moiety, an ethyleneoxide moiety, a polymer formed from repeating —(—$CH_2$—$CH_2$—O—)— moieties, such as polyethylene glycol (PEG), or polyethylene oxide (PEO), a polyamine, or a polyol. The spacer may be stable to thermolysis or hydrolysis or both. The spacer may be biocompatible, bioavailable, soluble and/or substantially soluble in aqueous and/or physiological medium, or combinations thereof. The biomolecule or biopolymer may comprise one or more spacer group residues, for example, such as a polyethylene glycol (PEG) or a polyethylene oxide group (PEO). The cross-linked protein matrix may comprise one or more spacer group residues, for example, such as a polyethylene glycol (PEG) or a polyethylene oxide group (PEO). The saccharide-containing molecule may comprise one or more spacer group residues, for example, such as a polyethylene glycol (PEG) or a polyethylene oxide group (PEO). The saccharide-containing molecule may comprise one or moieties that include a reactive group, for example, a reactive group that may form a covalent bond when reacted with a complementary reactive group that may be part of a protein or modified protein. The protein or modified protein may comprise one or moieties that include a reactive group, for example, a reactive group that may form a covalent bond when reacted with a complementary reactive group that may be part of a saccharide-containing molecule.

Degree of Modification of Polysaccharide

In certain embodiments, the saccharide-containing cross-linker, comprising one or more carboxyl and/or hydroxyl groups, for example, hyaluronic acid, may be activated and/or modified to comprise a range of activated and/or modified carboxyl and/or hydroxyl groups and a range of carboxyl and/or hydroxyl groups that are not activated and/or not modified. For example, the activated and/or modified saccharide-containing cross-linker may be activated and/or modified to comprise at least or about 2% of activated and/or modified carboxyl and/or hydroxyl groups, such as at least or about 0.5%, 1%, 3% 5%, 10%, 20%, 25%, 30%, or 35% of activated and/or modified carboxyl and/or hydroxyl groups. In certain applications, the saccharide-containing cross-linker may contain substantially or completely activated and/or modified carboxyl and/or hydroxyl groups. In certain embodiments, the activated and/or modified saccharide-containing cross-linker may be activated and/or modified to comprise between about 0.5% to about 40%, about 1% to about 30%, about 1% to about 25%, about 3% to about 30%, or about 5% to about 25%, activated and/or modified carboxyl and/or hydroxyl groups.

In certain embodiments, variance in the level of activated and/or modified groups in the saccharide-containing cross-linker may increase or decrease the ability of the saccharide-containing cross-linker to cross-link with a biomolecule. For example, the level of activated and/or modified groups in the saccharide-containing cross-linker may result in the formation of one or more connections between the saccharide-containing cross-linker and the biomolecule or biopolymer. Variance in the level of saccharide-containing cross-linker comprising activated and/or modified groups employed to prepare the cross-linked protein may control or substantially control the number of activated and/or modified groups capable of reacting with a biomolecule or biopolymer, such as linking and/or cross-linking with a protein, may stabilize or substantially stabilize the protein.

Extruding

In certain embodiments, the cross-linked protein matrix may be extruded through a needle. For example, extruded through a fine gauge needle. The cross-linked protein matrix may retain sufficient cohesiveness, for example, retain sufficient cohesiveness even after needle extrusion such that a long string of material may be extruded from the needle without the material breaking. For example, such as a string of material of at least of about 15 cm may be extruded from the needle without the material breaking. The cross-linked protein matrix may comprise a flexible matrix structure. For example, the flexible matrix structure of the cross-linked protein matrix may facilitate the production of firm biomaterials that retain sufficient flexibility to be ejected through a fine needle. In certain embodiments, a formulation comprising a cross-linked protein matrix may be extruded through a needle, for example, extruded through a fine gauge needle without the need for further processing. In certain embodiments, a formulation comprising a cross-linked protein matrix may retain sufficient cohesiveness even after needle extrusion such that a long string of material may be extruded from the needle without the material breaking, such as a string of material of at least of about 15 cm. In certain embodiments, a formulation may comprise a cross-linked protein matrix comprising flexible matrix structure. For example, in certain embodiments, the flexible matrix structure of the cross-linked protein matrix in the formulation may facilitate the production of firm biomaterials, such as firm biomaterials that retain flexibility, for example, substantial and/or sufficient flexibility, and may allow the formulation and/or biomaterial to be ejected through a needle, for example, a fine gauge needle.

Methods of Preparing

In certain embodiments, the concentration of a polysaccharide in the reaction may be between about 0.1% to about 5%, for example, between about 0.25% to about 3%, about 0.5% to about 3%, or about 0.25% to 3.5%.

In certain embodiments, the reagent stoichiometry may vary with the chemistry and polysaccharide chosen. For example, for HA:EDC:NHS, the ratio may be 1:1:1, 1:1:2, 1:1:3, 1:0.5:2, 1:0.5:3. With NHS the 1:1:1 ratio has been found to give good results in terms of NHS incorporation into a soluble polysaccharide cross-linking agent.

In certain embodiments, the molar ratio of polysaccharide to activating agent may be at least 1:1 to at least about 1:4. In certain embodiments, the molar ratio of the activating agent to the carboxylic acid units of the polysaccharide may be between about 2% to about 200%, for example, between about 5% to about 100%. In certain embodiments, the molar ratio of the modifying agent to the activating agent may be between about 1:1 to about 3:1, for example, between about 1.5:1 to about 2.5:1, such as about 2:1.

In certain embodiments, the pH for carrying out the preparation of the polysaccharide cross-linker reaction may be at least 4, 5, 6, 7, 8.0 or 8.5. In certain embodiments, the pH for carrying out the preparation of the polysaccharide cross-linker reaction may be between about 5 to about 15, about 6.5 to about 9, about 7 to about 8.6. Other pHs may also be used.

In certain embodiments, the temperature range of the activation, coupling, and/or cross-linking reaction is conducted at a temperature of between about 15° C. to about 30° C., 20° C. to about 25° C., or at room temperature.

In certain embodiments, the method of purifying and/or isolating the derivatized polysaccharide may be robust, simple, high yielding, or combinations thereof. For example, the method may yield at least 40% isolated derivatized polysaccharide, with respect to starting polysaccharide. In other methods, the yield may be at least 40%, 50%, 60%, 65%, 70%, 75%, 80%, 85%, 90% or 95% isolated derivatized polysaccharide, with respect to starting polysaccharide or modified polysaccharide.

Therapeutic Uses

The cross-linked protein matrix compositions, materials, formulations, methods of use, systems and/or kits disclosed herein may be employed in various therapeutic settings, including but not limited to, employed in human or veterinary medicine, such as in surgery. For example, they may be employed therapeutically in restorative surgery, aesthetic surgery, aesthetics, tissue bulking, such as incontinence or in dermal replacement products, dermatology, such as dermatological surgery, eye surgery, rheumatology, pharmacology, or in the field of cosmetics. Other therapeutic uses may include stemming hemorrhage in general surgery, reconstructing nerves and vessels in reconstructive, neuro- and plastic surgery, and anchoring skin, vascular, or cartilage transplants or grafts in orthopedic, such as treating knee osteoarthritis (inflammatory knee), vascular, and plastic surgery. Certain embodiments may be useful as vehicles for the delivery of cells or bioactive molecules such as growth factors to stimulate focal repair; local delivery of growth factors in combination with the cross-linked protein matrix compositions, materials, and/or formulations may facilitate wound healing and tissue regeneration in many situations, such as in promoting bone formation, stimulating cartilage repair in orthopedic procedures, treating pathological wound conditions, such as chronic ulcers, and/or serve as a scaffold to generate artificial tissues through proliferation of autologous cells in culture. In certain embodiments, the injectable nature of the cross-linked protein matrix compositions, materials, and/or formulations may render it suitable for tissue augmentation in plastic surgery, for example, as an inert biocompatible filler material, such as for filling dermal creases or for lip reconstruction. In certain embodiments, the cross-linked protein matrix compositions, materials, and/or formulations may be useful for supplementation of a body cavity or a deficit. In certain embodiments, the cross-linked protein matrix compositions, materials, and/or formulations may be useful in aesthetic medicine, orthopedic treatment, restoring volume effused during surgery, such as during eye surgery, and/or topical application on healthy or injured tissue, such as skin, for example, topical application in cosmetology and/or dermatology. In certain embodiments, the cross-linked protein matrix compositions, materials, and/or formulations may be useful in filling facial wrinkles, fine lines, treatment of "aging" skin, scarred tissue, and/or skin depressions, such as lipodystrophy.

Certain embodiments may be used to stabilize a protein, for example, a bioactive protein, utilized to deliver one or more stabilised proteins, for example, one or more bioactive proteins.

Certain embodiments may include a pharmaceutical active substance dispersed throughout and may be useful as a drug delivery system. Certain embodiments may include, for example, proteins, growth factors, enzymes, drugs, biopolymers, biologically compatible synthetic polymers, and/or combinations, derivatives, or variations thereof.

Characteristics; Stability

In certain embodiments, the cross-linked protein matrix may comprise at least one of the following properties, including but not limited to, injectable, biocompatible, substantially biocompatible, stable, substantially stable, maintains bioactivity, substantially maintains bioactivity, maintains bioactive conformation, provides elasticity or substantial elasticity, an elastic modulus, a viscous modulus, provides structural rigidity or substantial rigidity, resistance or substantial resistance to heat, resistance or substantial resistance to thermolysis, resistance or substantial resistance to biodegradation, may be biodegradable, may not elicit a foreign body response or a pronounced foreign body response (i.e., self recognition), has a purity level of at least about 25%, extrudable, extrudable through a needle, extrudable through a fine gauge needle.

In certain embodiments, the cross-linked protein matrix composition, material, and/or formulation may comprise a saccharide-containing molecule having at least one of the following properties, including but not limited to, substantial solubility, aqueous solubility, substantially soluble in an aqueous solution and/or an aqueous buffer solution, physiological solubility, substantial physiological solubility, injectable, biocompatible, substantially biocompatible, stable, substantially stable, maintains bioactivity, substantially maintains bioactivity, maintains bioactive conformation, resistance or substantial resistance to biodegradation, may be biodegradable, may not elicit a foreign body response or a pronounced foreign body response (i.e., self recognition), or has a purity level of at least about 25%.

In certain embodiments, the cross-linked protein matrix composition, material, and/or formulation may have and/or comprise having at least one of the following properties, including but not limited to, injectable, biocompatible, substantially biocompatible, stable, substantially stable, maintains bioactivity, substantially maintains bioactivity, maintains bioactive conformation, provides elasticity or substantial elasticity, an elastic modulus, a viscous modulus, provides structural rigidity or substantial rigidity, resistance or substantial resistance to heat, resistance or substantial resistance to thermolysis, resistance or substantial resistance to biodegradation, may be biodegradable, may not elicit a foreign body response or a pronounced foreign body response (i.e., self recognition), has a purity level of at least about 25%, extrudable, extrudable through a needle, or extrudable through a fine gauge needle.

Certain embodiments may have an elastic modulus of between about 500 Pa to about 50 Pa, about 450 Pa to about 100 Pa, about 400 Pa to about 125 Pa; about 400 Pa to about 150 Pa, or about 385 Pa to about 150 Pa. The elastic modulus will vary depending on the concentration and components used. For example, for a 1% HA cross-linked 4% tropoelastin matrix product the elastic/storage modulus is stable across a range of frequencies at around 80-100 Pa and dominates the material with the loss modulus starting around 5-10 Pa and gradually increasing with increasing angular frequencies.

Certain embodiments may have an extrudable length, that is substantially coherent and substantially holds together without support, of at least about 5 cm, 10 cm, 12 cm, 15 cm, 18 cm, 20 cm, or 25 cm when extruded through a 25 G needle. Certain embodiments may have an extrudable length, that is coherent and holds together without support, of at least about 5 cm, 10 cm, 12 cm, 15 cm, 18 cm, 20 cm, or 25 cm when extruded through a 25 G needle.

Certain embodiments may have an extrudable length, that is substantially coherent and substantially holds together without support, of at least about 5 cm, 10 cm, 12 cm, 15 cm, 18 cm, 20 cm, or 25 cm when extruded through a 27 G needle. Certain embodiments may have an extrudable length, that is coherent and holds together without support, of at least about 5 cm, 10 cm, 12 cm, 15 cm, 18 cm, 20 cm, or 25 cm when extruded through a 27 G needle.

Certain embodiments may have an extrudable length, that is substantially coherent and substantially holds together without support, of at least about 5 cm, 10 cm, 12 cm, 15 cm, 18 cm, 20 cm, or 25 cm when extruded through a 30 G needle. Certain embodiments may have an extrudable length, that is coherent and holds together without support, of at least about 5 cm, 10 cm, 12 cm, 15 cm, 18 cm, 20 cm, or 25 cm when extruded through a 30 G needle.

Certain embodiments may have an extrudable length, that is substantially coherent and substantially holds together without support, of at least about 5 cm, 10 cm, 12 cm, 15 cm, 18 cm, 20 cm, or 25 cm when extruded through a 31 G needle. Certain embodiments may have an extrudable length, that is coherent and holds together without support, of at least about 5 cm, 10 cm, 12 cm, 15 cm, 18 cm, 20 cm, or 25 cm when extruded through a 31 G needle.

Certain embodiments may have an extrudable length of at least about 5 cm, 10 cm, 12 cm, 15 cm, 18 cm, 20 cm, or 25 cm through a fine gauge needle. Certain embodiments may have an extrudable length between about 5 cm to about 30 cm, about 10 cm to about 20 cm; about 10 cm to about 15 cm, or about 15 cm to about 30 cm. Certain embodiments may have an extrudable length, that is substantially coherent and substantially holds together without support, of at least about 5 cm, 10 cm, 12 cm, 15 cm, 18 cm, 20 cm, or 25 cm through a fine gauge needle. Certain embodiments may have an extrudable length, that is coherent and holds together without support, of at least about 5 cm, 10 cm, 12 cm, 15 cm, 18 cm, 20 cm, or 25 cm through a fine gauge needle. Certain embodiments may have an extrudable length between about 5 cm to about 30 cm, about 10 cm to about 20 cm; about 10 cm to about 15 cm, or about 15 cm to about 30 cm that is substantially coherent and substantially holds together without support when extruded.

In certain embodiments, the cross-linked protein matrix composition, material, and/or formulation may be stabilized by the protein component of the product. The stability of the cross-linked protein matrix composition, material, and/or formulation may result from a combination of a full length protein residue component and a cross-linking residue component, such as a polysaccharide residue component. In certain embodiments, the properties of a final material may not depend on the viscosity of the polysaccharide residue component, such as the starting polysaccharide molecular component. The cross-linked protein matrix composition, material, and/or formulation may be stabilized by the cross-linking residue component of the product, such as a saccharide-containing cross-linking residue, for example, a polysaccharide cross-linker residue.

In certain embodiments, the cross-linked protein matrix composition, material, and/or formulation comprises a biocompatible cross-linked protein residue.

In certain embodiments, the cross-linked protein matrix composition, material, and/or formulation may be suitable for incorporation in a syringe.

In certain embodiments, fine gauge needles may be used. For example, 25 G, 27 G, 29 G, 30 G or 31 G needles may be used. However, certain embodiments may be used with larger gauge needles, for example, 20 G to 25 G, 15 G to 25 G, 15 G to 20 G, 10 G to 20 G, 10 G to 15 G, etc. In certain embodiments, the size of the needle may depend on the material injected, for example, the type and/or consistency of the material injected, on the desire to deliver a particular amount of volume of material and/or combinations or variations thereof. Certain embodiments enable the use of fine gauge needles where the disclosed formulation retains sufficient cohesiveness after needle extrusion such that >15 cm long strings of material can be extruded from the needle without the material breaking. For example, with certain embodiments >15 cm long strings of material can be extruded from the 25 G, 27 G, 29 G, or 30 G needle without the material breaking.

For certain applications, for example, bulking applications such as the bladder neck a needle of 18, 19, 20, 21, 22, or 23 G may be used. Broader needles may be used in certain applications as the needle length is longer (usually several inches) and so flow through the needle is subject to more resistance. In certain applications, the volume to be injected may also be increased by several milliliters, for example, at least 1.5 ml, 2 ml, 2.5 ml, 3 ml, or 4 ml. In certain applications, where lower volume may be used, (for example, 'threading' or filling of fine wrinkles or thin skin augmentation) the volume used may be less, for example, less than 2 ml, 1.5 ml, 1.0 ml, 0.75 ml, 0.5 ml or 0.1 ml. Typically, these applications use a shorter narrow gauge needle, for example, 29 G, 30 G or 31 G that is ½ inch in length.

The gauge of the needle and length of needle used may vary depending on the particular application and/or the formulation. For example, formulations with higher levels of derivatization (e.g., 20-30% of possible sites modified, 1.5% polysaccharide and 5% protein content) which may be used to provide more structural persistent tissue support would typically be applied using a short broader needle (such as 27 or 25 G×½" or 1"). Another example, would be a formulation with low derivatization (around 5%), low HA (<1%) and/or protein (<3%) that would typically be delivered through a finer needle such as a 31 G needle.

In certain embodiments, the extruded material may be extruded without support—usually extruded from an initial surface vertically or at an angle of 45° from vertical. The ability to form coherent threads of material may make it particularly attractive for applications where threading of the implant is carried out in the skin in a matrix or lattice to provide structural support.

Other methods of delivery may also be used, for example, cannulas, catheters, flexible polymer catheters, and/or syringes with no needle.

In certain embodiments, at least one of the benefits of the methods and/or cross-linked protein matrix compositions, materials, and/or formulations disclosed herein, is that the amount of protein that may be included in the resulting material formulation is not a limiting factor. For example, the protein residue content included in the cross-linked protein matrix may comprise about 35 or 40 mg/ml above the amount in which they may become resistant to needle extrusion when using other methods of cross-linking proteins such as chemical cross-linkers such as glutaraldehyde (as the cross linked material may be quite dense). The protein residue may be cross-linked intra-molecularly, inter-molecularly, and/or combinations thereof. The protein residue may be substantially or only cross-linked inter-molecularly. The cross-linked protein matrix formulation may be more flexible and/or may be amenable to injection at high protein concentrations.

The cross-linked protein matrix compositions, materials, and/or formulations disclosed herein may be utilized in a kit or package. In certain embodiments, the kit or package comprises a syringe that has been pre-filled with the cross-linked protein matrix composition and an assortment of appropriate size needles or needle delivery systems, such as a needle roller ball type system, an automatic injection pen type system or a mesotherapy injection gun type system. The package or kit may also contain instructions for injecting the provided composition. In other embodiments, the kit or package may comprise at least one syringe, at least one separate container such as a vial or ampoule that contains the composition to be used, multi-needles, and instructions on how to use the kit.

EXAMPLES

The following examples and protocols are given as particular embodiments of the disclosure and to demonstrate the advantages thereof. It is understood that the examples and protocols are given by way of illustration and are not intended to limit the specification or the claims that follow.

Procedure for Derivatisation of Hyaluronic Acid (HA) using EDC and NHS:
1. Dissolve HA in water to a final concentration of 1% (possibly up to 2%).
2. Add 1 g of N-hydroxysuccinimide (NHS) per g of HA to be derivatized.
3. Add 1 g of 1-Ethyl-3-(3-dimethylaminopropyl)-carbodiimide (EDC) per gram of HA.
4. Ensure reactants are completely dissolved by thorough stirring (approx. 10-20 mins).
5. React for 60 min at 20-25° C.
6. Add NaCl to a final concentration of 1%.
7. Precipitate derivatised HA by the addition of 2 Volumes of isopropanol (IPA).
8. Recover precipitated derivatised HA by filtration, gentle centrifugation or other suitable means and discard the supernatant.
9. Gently press the recovered derivatised/HA to remove excess liquid
10. Wash Precipitated derivatised HA in 60% IPA.
11. Remove and discard the wash fluid.
12. Gently press the recovered derivatised HA to remove excess liquid.
13. Weigh the amount of recovered derivatised/HA.
14. Dissolve the recovered derivatised/HA in sterile water to a final concentration of 2.5% based on the initial amount of HA dissolved in step 1.
15. Analyse the amount of NHS derivitisation (based on chemical modification and UV analysis).
16. Analyse the concentration of dissolved derivatised HA (based on chemical modification and UV analysis or dry weight).
17. Adjust concentration of derivatised HA to 2% (20 mg/ml).
18. Sterile filter the derivatised HA.

Note: Step 7-14 should be conducted as quickly as possible, for example, less that 30 min should be allowed for these steps in total (though, actual dissolution of precipitated HA may take longer).

Procedure for Preparation of Cross-Linked Protein Matrix
1. Dissolve protein in sterile PBS to a final concentration of 100 mg/ml and filter sterilise.
2. Analyse protein concentration (e.g., based on UV analysis).
3. Mix equal volumes of 20 mg/ml derivatised HA with 100 mg/ml protein under thorough mixing/stirring without introduction of any air bubbles.
4. Leave to gel for 30-60 minutes (20-25° C.).
5. Fill in syringes.

Following are common procedures used in the Examples that follow.

Example 1

Schematic Diagram for a Production of a Soluble Hyaluronic Acid Cross Linker Using a Carbodiimide and N-Hydroxysuccinimide (NHS)

Hyaluronic Acid (HA) is a polysaccharide consisting of β-D-glucuronic acid-[1□3]-β-D-N-acetyl-glucosamine disaccharide units. The ideal structure of HA is shown in FIG. 1.

Figure 2:
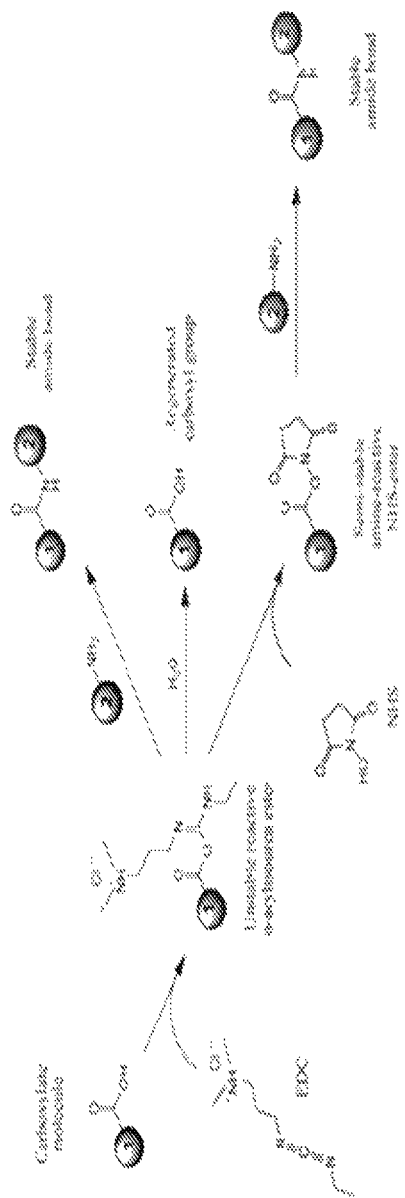
FIG. 2 illustrates, in accordance with certain embodiments, a Reaction Mediated by EDC and NHS with a Carboxylate-Containing Molecule (1) and an amine (2) possible intermediate structures illustrated include an O-acylisourea ester and an NHS ester intermediate, formed from a modifying agent, such as N-hydroxysuccinimide (NHS), to form an NHS activated carboxylate intermediate that is capable of reacting with a primary amino group (1) to form an amide bond.

As can be seen, HA contains one carboxyl group per disaccharide unit, and it is this functional group that may be utilised in the at least one of the cross-linking approaches disclosed herein. In this approach a covalent chemical bond between the carboxyl group of the HA and the free amino groups of the protein is formed. This can be done by reacting the HA with a carbodiimide such as 1-Ethyl-3-(3-dimethylaminopropyl)-carbodiimide (EDC), forming an active o-acylisourea ester. While this compound is reactive with nucleophiles such as primary amino groups, it is also unstable and will hydrolyze quickly in water in the absence of any suitable reactive groups. It is therefore often preferred to form a more stable intermediary active ester from the active o-acylisourea ester, which can be effected by a condensation reaction using compounds such as N-hydroxysuccinimide (NHS) or Sulfo-N-hydroxysuccinimide (Sulfo-NHS). This results in the formation of NHS activated HA, which then can react with primary amino groups from the protein to form very stable amide bonds. Schematics of these reactions are shown in FIG. 2.

One of the main benefits of this approach is that the HA can be derivatised prior to being mixed with the protein, which will limit or avoid the presence of residual derivatising reagents in the final formulation. The main approaches for removal of the excess reagents are either precipitation with water miscible organic solvents such as isopropyl alcohol (IPA) or ethanol followed by washing with a water/solvent mixture or diafiltration using a semipermeable membrane with a suitable molecular weight cut-off. Once the derivatised HA has been purified it can then be dissolved in water or an appropriate buffer such as phosphate buffered saline (PBS) and then be mixed with protein to form a cross-linked formulation through reaction between the NHS activated carboxylic acids of the HA and the amino groups from the protein. In this approach the HA effectively becomes the cross-linker for the protein. The properties of the resulting formulation are expected to be different to a formulation where the protein is cross-linked with a short cross-linker; or, where the HA is cross-linked by a short cross-linker in the absence of a protein.

Example 2

Schematic Diagram for a Production of a Soluble Hyaluronic Acid Cross Linker Using the Heterobifunctional Reagent Allylglycidyl Ether (AGE)

This approach is based on derivatising Hyaluronic Acid (HA) with a heterobifunctional reagent that allows for a two-step approach for the cross linking of proteins with HA. The method chosen in this Example was the use of allyl-glycidyl ether (AGE), where the initial incorporation of AGE happens when the oxirane group reacts with the hydroxyl groups of the HA under strongly alkaline conditions, forming a stable ether bond. The allyl groups thus incorporated can then be converted into halohydrins by reaction with a halide such as bromine. These halohydrins can then react with protein through primary amino groups by forming stable secondary amine bonds. The reaction between halohydrins and primary amino groups happens more efficiently at high pH values, but some reaction will begin to occur above pH 8.5-9.

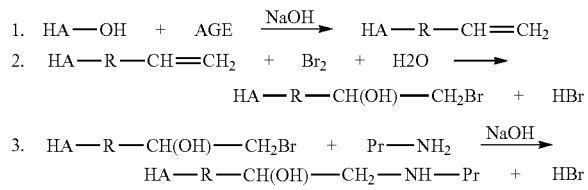

The reaction scheme shown above for the cross linking Proteins with HA. HA=Hyaluronic Acid, R=O—CH$_2$—CH(OH)—CH$_2$—O—CH$_2$, AGE=AllylGlycidyl Ether, Pr=Protein.

Example 3

Preparation of a Polysaccharide Cross-Linker A

In this Example, 5 ml of a 1% low molecular weight hyaluronic acid solution, 1 ml H$_2$O, 100 mg NHS (Sigma) and 100 mg EDC (Sigma) were mixed together and allowed to react for 1 hour at room temperature. The derivatised hyaluronic acid was then precipitated with two volumes of IPA, pressed briefly to reduce water and solvent content of precipitate, washed with 66% Ethanol then re-dissolved in 4 ml phosphate buffered saline (Sigma) at room temperature. The derivatised HA dissolved completely within 1 hour. The concentration of the derivatised HA was measured using a moisture analyser and then diluted to a 2% solution prior to use in protein cross-linking. All preparations were sterile and the experiments were, where possible, conducted in a laminar flow hood.

Example 4

Preparation of a Polysaccharide Cross-Linker B

In this Example, 5 ml of a 1% carboxymethyl cellulose solution, 1 ml H$_2$O, 100 mg NHS (Sigma) and 100 mg EDC (Sigma) were mixed together and allowed to react for 1 hour at room temperature. The derivatized carboxymethyl cellulose was then precipitated with two volumes of IPA, pressed briefly to reduce water and solvent content of precipitate, washed with 66% Ethanol then re-dissolved in 4 ml phosphate buffered saline (Sigma) at room temperature. All preparations were sterile and the experiments were, where possible, conducted in a laminar flow hood.

Example 5

Preparation of a Polysaccharide Cross-Linker C

In this Example, 4 ml 2% HA was mixed with 0.5 ml 10M NaOH and 0.5 ml AGE and left to react for 1 hour at room temperature. The solution was then neutralised with 1 ml 9M acetic acid, 40 mg of NaCl was added followed by precipitation with 2 volumes IPA. The precipitate was washed with 60% IPA, padded dry on filter paper and then redissolved in 3 ml water. The incorporated allyl groups were then converted with bromine water (250 µL was added, but the amount necessary for full conversion was between 200 and 250 µL). To remove excess bromine, the solution was re-precipitated by adding 30 mg NaCl followed by 2 volumes IPA. The precipitate was washed with 60% IPA, padded dry on a filter paper and then re-dissolved in 2 ml water. 0.5 ml of the solution was used to test the final concentration of derivatised HA in a moisture analyser and the dry matter content was found to be 2.59%. The derivatised HA was diluted to a 2% solution prior to use in protein cross-linking.

Example 6

Preparation of a Protein Based Formulation Using rh Tropoelastin 1

In this Example, 250 µL of a 200 mg/ml rh tropoelastin solution in phosphate buffered saline (Elastagen) was mixed with 250 µL phosphate buffered saline followed by the addition of 500 µL of the hyaluronic acid cross linker of Example 3. The combination was mixed thoroughly followed by brief centrifugation to remove air bubbles. The material was left for 30 min at room temperature to formulate. The formulation was then filled into a sterile 1 ml syringe in a laminar flow hood. The formulations made in this way all presented with the properties of firm materials which were extrudable through fine gauge 31 G needles as coherent threads of 10-20 cm in length.

Example 7

Preparation of a Protein Based Formulation Using Bovine Serum Albumin (BSA)

In this Example, 250 µL of a 200 mg/ml BSA solution in phosphate buffered saline (Sigma) was mixed with 250 µL phosphate buffered saline followed by the addition of 500 μL of the hyaluronic acid cross linker of Example 3. The combination was mixed thoroughly followed by brief centrifugation to remove air bubbles. The material was left for 30 min at room temperature to formulate. The formulation made in this way presented with the properties of a firm material which was extrudable through fine gauge 31 G needles as coherent threads of 10-20 cm in length.

Example 8

Preparation of a Protein Based Formulation Using rhHSA

In this Example, a 20 mg/ml solution of recombinant HSA (Sigma) in phosphate buffered saline (Sigma) was mixed with an equal volume of the hyaluronic acid cross linker of Example 3. The combination was mixed thoroughly followed by brief centrifugation to remove air bubbles. The material was left for 30 min at room temperature to formulate. This produced a soft cross-linked clear colourless HSA formulation which was extrudable through fine gauge 31 G needles.

Example 9

Preparation of a Protein Based Formulation Using rh Tropoelastin 2

In this Example, 500 μL of a 100 mg/ml rh tropoelastin solution in phosphate buffered saline (Elastagen) was mixed with 500 μL of 2% hyaluronic acid cross linker of Example 5 at pH 8.5. The combination was mixed thoroughly followed by brief centrifugation to remove air bubbles. The material was left for 12 hours at room temperature to formulate. The formulation produced was a firm clear colourless matrix formulation of HA cross-linked tropoelastin.

Example 10

Assessment of Monomer Content in Formulations

Figure 3:
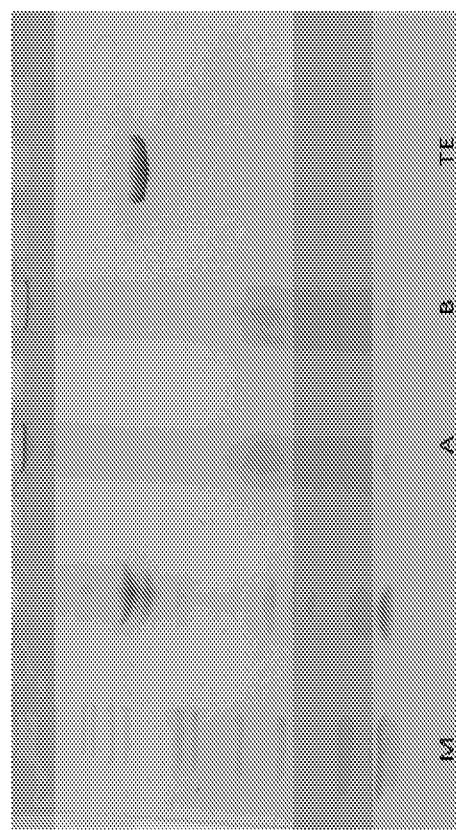
FIG. 3 illustrates, in accordance with certain embodiments, an SDS PAGE Gel of Protein Extracted from the Formulation of Example 5 that was soaked in PBS, containing the following lanes: Marker (lane M); Supernatant (lanes A and B); and pure TE (lane TE).

In this Example, an aliquot of the formulation produced in Example 6 was soaked in PBS and the resulting supernatant was analysed by SDS-PAGE (the resulting gel is illustrated in FIG. 3).

Loading: Formulation Produced in Example 6, soaked in PBS
Lane M: Marker.
Lanes A and B: Supernatant.
Lane TE: Pure TE.
As can be seen from the gel, no monomer was extracted from the HA-TE preparation.

Example 11

Assessment of Formulation Rheology

In this Example, the rheological behavior in shear flows of the formulation produced in Example 6 was studied using a Haake RS150 rheometer utilizing a cone and plate geometry. A 35 mm/1° Titanium cone was used in the study with temperature maintained at 25° C.

The response of the formulation to small amplitude oscillatory shear flow, with varying angular frequency, is dominated by the storage modulus (G') in the angular frequency range of 0.1 and 100 rad/s. Over this range the storage modulus was relatively insensitive to changes in angular frequency. In steady shear flow, the strain increases linearly with stress up to about 200 Pa. Beyond this value a small change in applied stress led to a significant increase in strain, When the shear viscosity was plotted against shear rate the fluid demonstrated a constant viscosity of around 260 Pas at low shear rates. The viscosity however rapidly decreased with increasing shear rate beyond a shear rate of about 0.4/s.

The rheological properties of the protein based formulation produced at Example 6 are significantly different from uncross-linked polysaccharides and from polysaccharide products cross-linked with short cross-linkers such as BDDE which are then micronized to enable fine needle extrusion. These polysaccharide products behave more like viscous fluids and have a greater contribution to their rheological properties from the loss modulus (G") over the same frequencies examined. The relatively constant value of the complex modulus of the formulation produced in Example 6 provides a particular point of difference to polysaccharide based products.

In the following, further embodiments or examples are provided:

Embodiment 1

A composition, comprising at least one cross-linked protein matrix, wherein the at least one cross-linked protein matrix comprises:
  i) at least one protein residue; and
  ii) at least one saccharide-containing residue.
2. The composition of embodiment 1, wherein the composition is an injectable composition.
3. The composition of embodiments 1 or 2, wherein the composition is delivered by cannular, catheter, flexible polymer catheter, syringe with needle, or syringe without needle.
4. The composition of one or more of embodiments 1-3, wherein the composition is extrudable to a length of at least 10 cm.
5. The composition of one or more of embodiments 1-4, wherein the composition is extrudable through needles of 18 G to 31 G to a length of between about 5 cm to about 30 cm and the extruded composition substantially holds together without surface support.
6. The composition of one or more embodiments 1-5, wherein the composition is extrudable through a 25 G needle to a length of at least 5 cm, 10 cm, 12 cm, 15 cm, 18 cm, 20 cm, or 25 cm.
7. The composition of one or more of embodiments 1-6, wherein the composition is extrudable to length of at least 10 cm, 15 cm, 20 cm, or 25 cm when extruded through a fine gauge needle.
8. The composition of one or more of embodiments 1-7, wherein the composition is extrudable to a length of between 5 cm to 30 cm, 10 cm to 20 cm; or 15 cm to 30 cm without further surface support when extruded through a fine gauge needle and wherein the extruded composition is substantially coherent and substantially holds together.
9. The composition of one or more of embodiments 1-8, wherein the composition is extrudable to a length of at least 10 cm, 15 cm, 20 cm, or 25 cm without additional physical support when extruded through a medium gauge and the extruded composition is substantially coherent and substantially holds together.

10. The composition of one or more embodiments 1-9, wherein the composition is extrudable to a length of at least 10 cm, 15 cm, 20 cm, or 25 cm without further surface support when extruded through a large gauge needle and the extruded composition is substantially coherent and substantially holds together.

11. The composition of one or more of embodiments 1-10, wherein the composition is extrudable to a length of at least 10 cm, 20 cm, or 30 cm without further surface support at an angle of at least 45° from vertical and forms coherent threads of material.

12. The composition of one or more of embodiments 1-11, wherein the extruded composition forms coherent threads of material.

13. The composition of one or more of embodiments 1-12, wherein the composition can be extruded without substantial further processing.

14. The composition of one or more of embodiments 1-13, wherein the composition can be extruded without substantial further processing through a fine gauge needle and when extruded is substantially coherent and substantially holds together without further physical support.

15. The composition of one or more of embodiments 1-14, wherein the composition retains sufficient cohesiveness after needle extrusion such that strings of extruded composition do not break during extrusion.

16. The composition of one or more of embodiments 1-15, wherein the composition retains sufficient cohesiveness after needle extrusion such that strings of the composition greater than 10 cm, greater than 12 cm, greater than 15 cm, greater than 18 cm or greater than 20 cm can be extruded from the needle without the strings of the composition breaking.

17. The composition of one or more of embodiments 1-16, wherein the at least one cross-linked protein matrix comprises a full length protein residue.

18. The composition of one or more of embodiments 1-17, wherein the at least one cross-linked protein matrix comprises a substantially full length protein residue.

19. The composition of one or more of embodiments 1-18, wherein the composition is substantially flexible such that it may be ejected through a needle.

20. The composition of one or more of embodiments 1-19, wherein the composition has sufficient flexibility to allow ejection through fine gauge needles.

21. The composition of one or more of embodiments 1-20, wherein the composition enables the at least one protein residue to retain its full length, or substantially full length, and the at least one protein residue is protected from rapid resorption or breakdown.

22. The composition of one or more of embodiments 1-21, wherein the composition enables the at least one protein residue to retain its full length, or substantially full length, and wherein the composition is needle injectable, retains a coherent structure, and is sufficiently cross-linked to slow the composition's resorption in vivo.

23. The composition of one or more of embodiments 1-22, wherein the at least one protein residue is substantially full length and substantially devoid of intramolecular cross-links.

24. The composition of one or more of embodiments 1-23, wherein the composition is tissue compatible, enhances tissue in-growth, enhances tissue re-growth, or combinations thereof 25. The composition of one or more of embodiments 1-24, wherein the composition may be remodeled into typical and desirable structures and incorporated into new tissue.

26. The composition of one or more of embodiments 1-25, wherein the at least one saccharide-containing residue remains soluble, or sufficiently soluble, in water or saline solution.

27. The composition of one or more of embodiments 1-26, wherein the at least one saccharide-containing residue is substantially soluble in an aqueous or physiological medium.

28. The composition of one or more of embodiments 1-27, wherein the at least one cross-linked protein residue is substantially intermolecularly cross-linked.

29. The composition of one or more of embodiments 1-28, wherein the at least one saccharide-containing residue has one or more of the following properties: substantially bioavailable, substantially biodegradeable, substantially bioabsorbable, or substantially bioresorbable.

30. The composition of one or more of embodiments 1-29, wherein the at least one saccharide-containing residue comprises at least one polysaccharide residue, at least one oligosaccharide residue or combinations thereof.

31. The composition of one or more of embodiments 1-30, wherein the at least one polysaccharide residue comprises a low, medium, high molecular weight polysaccharide residue or combinations thereof.

32. The composition of one or more of embodiments 1-31, wherein the at least one polysaccharide residue comprises a molecular weight of between about 50,000 to about 275,000 Daltons.

33. The composition of one or more of embodiments 1-32, wherein the at least one polysaccharide residue is derived from or comprises the residue of hyaluronic acid, a cellulose derivative, carboxy cellulose, carboxymethyl cellulose, hydroxymethyl cellulose, hydroxypropyl cellulose, hydroxypropyl methylcellulose, hydroxy-propylcellulosecarboxymethyl amylose, xanthan gum, guar gum, α-glucan, β-glucan, β-1,4-glucan, β-1,3-glucan, alginates, carboxymethyl dextran, a glycosaminoglycan derivative, chondroitin-6-sulfate, dermatin sulfate, heparin, heparin sulfate, polylactic acid, polyglycolic acid, poly(lactic-co-glycolic) acid, tricalcium phosphate, 1-hydroxyapatite, pharmaceutically acceptable salts of derivatives of, or combinations thereof.

34. The composition of one or more of embodiments 1-33, wherein the at least one polysaccharide residue is derived from or comprises the residue of hyaluronic acid.

35. The composition of one or more of embodiments 1-34, wherein the at least one polysaccharide residue is derived from or comprises the residue of carboxymethyl cellulose.

36. The composition of one or more of embodiments 1-35, wherein the at least one cross-linked protein matrix comprises the at least one saccharide-containing residue in a concentration of between about 0.01% to about 30%.

37. The composition of one or more of embodiments 1-36, wherein the at least one protein residue comprises an amine-bearing side chain residue, comprising at least one lysine residue, at least one arginine residue, or combinations thereof.

38. The composition of one or more of embodiments 1-37, wherein the at least one protein residue is derived from or comprises the residue of tropoelastin, elastin, albumin, collagen, collagen monomers, immunoglobulins, insulin, derivatives of, or combinations thereof.

39. The composition of one or more of embodiments 1-38, wherein the amount of the at least one protein residue is between about 1 mg/ml to about 200 mg/ml.

40. The composition of one or more of embodiments 1-39, wherein the at least one cross-linked protein matrix comprises a bioactive protein residue.
41. The composition of one or more of embodiments 1-40, wherein the at least one cross-linked protein matrix is derived from or comprises the reside of a synthetic protein substantially identical to a naturally occurring human protein.
42. The composition of one or more of embodiments 1-41, wherein the at least one cross-linked protein matrix is derived from or comprises the residue of a stabilized protein.
43. The composition of one or more of embodiments 1-42, wherein the at least one cross-linked protein matrix is derived from or comprises the residue of an extra cellular protein.
44. The composition of one or more of embodiments 1-43, wherein the extra cellular protein is tropoelastin, elastin, collagen or a derivative thereof
45. The composition of one or more of embodiments 1-44, wherein the at least one cross-linked protein matrix comprises the at least one saccharide-containing residue in a concentration of between about 0.1% to about 5%.
46. The composition of one or more of embodiments 1-45, wherein the at least one cross-linked protein matrix comprises a ratio of about 0.1% to about 1.5% of the at least one saccharide-containing residue to about 0.1% to about 6% of the at least one protein residue.
47. The composition of one or more of embodiments 1-46, wherein the at least one cross-linked protein matrix comprises a ratio of about 0.1% to about 1.5% of the at least one saccharide-containing residue, comprising a polysaccharide residue, to about 0.1% to about 6% of the at least one protein residue.
48. The composition of one or more of embodiments 1-47, wherein the at least one cross-linked protein matrix is prepared from at least one saccharide-containing cross-linking molecule comprising at least 5%, 10%, 20%, or 25% of activated carboxyl and/or hydroxyl groups, modified carboxyl and/or hydroxyl groups or combinations thereof
49. The composition of one or more of embodiments 1-48, wherein the at least one cross-linked protein matrix is prepared from at least one saccharide-containing cross-linking molecule comprising at least 5% of activated carboxyl and/or hydroxyl groups, modified carboxyl and/or hydroxyl groups or combinations thereof.
50. The composition of one or more of embodiments 1-49, wherein the at least one cross-linked protein matrix comprises less than 5% of a monomeric protein residue.
51. The composition of one or more of embodiments 1-50, wherein the at least one cross-linked protein matrix comprises less than 1% of the monomeric protein residue.
52. The composition of one or more of embodiments 1-51, wherein the composition is employed therapeutically in at least one of the following: surgery, aesthetics, tissue bulking, treating incontinence, in dermal replacement products, dermatology, dermatological surgery, cosmetics or combinations thereof
53. The composition of one or more of embodiments 1-52, wherein the composition is employed therapeutically in deimatology.
54. The composition of one or more of embodiments 1-53, wherein the composition is employed therapeutically in deimatological surgery.
55. The composition of one or more of embodiments 1-54, wherein the composition is employed therapeutically as a topical application in cosmetology, dermatology or combinations thereof
56. The composition of one or more of embodiments 1-55, wherein the composition is employed therapeutically as a topical application in dermatology.
57. The composition of one or more of embodiments 1-56, wherein the composition is used for the treatment of facial wrinkles, the filling of facial wrinkles, the treatment of fine lines, the treatment of aging skin, the treatment of scarred tissue, treatment of skin depressions or combinations thereof.
58. The composition of one or more of embodiments 1-57, wherein the composition is employed in the implantation of a localized deposit of a substantially bioactive protein residue.
59. The composition of one or more of embodiments 1-58, wherein the composition is employed in the implantation of a localized deposit of a substantially bioactive protein residue.
60. The composition of one or more of embodiments 1-59, wherein the composition is employed in the implantation of slow release deposit of a substantially bioactive protein residue.
61. The composition of one or more of embodiments 1-60, wherein the at least one cross-linked protein matrix comprises at least 90%, 95%, 98% or 99% of the at least one protein residue cross-linked with a biomolecule and/or biopolymer, wherein the biomolecule and/or biopolymer comprises the at least one saccharide-containing residue.
62. The composition of one or more of embodiments 1-61, wherein the at least one cross-linked protein matrix comprises the at least one protein residue that is substantially cross-linked with a cross-linking biomolecule, biopolymer or combinations thereof.
63. The composition of one or more of embodiments 1-62, wherein the number of cross-links on the at least one polysaccharide residue may be at least 5%, 10%, 15%, 20%, or 25% of the number of possible cross-linking sites on the at least one polysaccharide residue.
64. The composition of one or more of embodiments 1-63, wherein the number of protein units not incorporated into the at least one cross-linked protein matrix and left unbound may be at least 1%, 3%, 5%, or 7%.
65. The composition of one or more of embodiments 1-64, wherein less than 20%, 15%, 10%, or 7% of the protein units are not incorporated into the at least one cross-linked protein matrix and left unbound.
66. The composition of one or more of embodiments 1-65, wherein the protein monomer may be cross-linked such that between about 90% to about 100% of the protein monomer may be incorporated into the composition.
67. The composition of one or more of embodiments 1-66, wherein the at least one protein residue is derived from a full length protein or a substantially full length protein and wherein the structure of the protein residue is not substantially masked by the at least one saccharide-containing residue.
68. The composition of one or more of embodiments 1-67, wherein the composition, comprising the at least one protein residue having a structure that is not substantially masked by the at least one saccharide-containing residue, may be more tissue compatible, enhance tissue in-growth, re-growth, or combinations thereof.
69. The composition of one or more of embodiments 1-68, wherein the composition, comprising the at least one protein residue having a structure that is not substantially masked by the at least one saccharide-containing residue, may be remodeled into more typical and desirable structures and/or incorporated into a new tissue.

70. A method of preparing the composition of one or more of embodiments 1-69, comprising cross-linking at least one protein with at least one soluble saccharide-containing molecule.

Embodiment 71

A method of preparing a composition, comprising at least one cross-linked protein matrix, wherein the at least one cross-linked protein matrix comprises:
  i) at least one protein residue; and
  ii) at least one saccharide-containing residue; wherein the cross-linking comprises:
    i) modifying the at least one saccharide-containing molecule to comprise at least one reactive chemical group;
    ii) combining the modified at least one saccharide-containing molecule with the at least one protein, wherein the at least one protein comprise a reactive chemical group complementary to the reactive group on the modified at least one saccharide-containing molecules; and
    iii) forming at least one bond between the at least one protein and the modified at least one saccharide-containing molecule.
72. The method of embodiments 70 or 71, wherein the at least one reactive chemical group is a chemical group that is capable of forming a covalent bond when combined with the at least one protein.
73. The method of one or more of embodiments 70-72, wherein the at least one bond is a covalent bond.
74. The method of one or more of embodiments 70-73, wherein the modified at least one saccharide-containing molecule is soluble or substantially soluble in water and/or saline solution.
75. The method of one or more of embodiments 70-74, wherein the modified at least one saccharide-containing molecule remains soluble or substantially soluble in water or physiological buffer.
76. The method of one or more of embodiments 70-75, wherein the at least one saccharide-containing molecule comprises a carboxyl and/or hydroxyl group.
77. The method of one or more of embodiments 70-76, wherein the at least one saccharide-containing molecule is modified by activating a carboxyl and/or hydroxyl group.
78. The method of one or more of embodiments 70-77, wherein the method may further comprise purifying the modified at least one saccharide-containing molecule by precipitation and/or filtration of the modified at least one saccharide-containing molecule to remove or substantially remove unreacted modification reactants.
79. The method of one or more of embodiments 70-78, wherein the modified at least one saccharide-containing molecule is used as a cross-linking agent when combined with the at least one protein.
80. The method of one or more of embodiments 70-79, wherein a solution of the modified at least one saccharide-containing molecule is mixed with the at least one protein to form the at least one cross-linked protein matrix.
81. A method of use comprising injecting the composition of one or more of embodiments 1-69.
82. The method of embodiment 81, wherein the injection is used to bulk, augment tissues or combinations thereof in at least one of the following: human or veterinary medicine; surgery; restorative surgery; aesthetic surgery; aesthetics; tissue bulking; dermatological surgery; eye surgery; rheumatology; pharmacology; in the field of cosmetics; stemming hemorrhage in general surgery; reconstructing nerves and vessels in reconstructive surgery, neurosurgery; plastic surgery; anchoring skin, vascular, or cartilage transplants or grafts in orthopedic surgery; treating knee osteoarthritis; vascular surgery; as vehicles for the delivery of cells or bioactive molecules, such as growth factors to stimulate focal repair; local delivery of growth factors in combination with the cross-linked protein matrix compositions to facilitate wound healing and tissue regeneration or promote bone formation; stimulating cartilage repair in orthopedic procedures; treating pathological wound conditions, such as chronic ulcers; serve as a scaffold to generate artificial tissues through proliferation of autologous cells in culture; for tissue augmentation in plastic surgery, such as for filling dermal creases or for lip reconstruction; for supplementation of a body cavity or a deficit; for aesthetic medicine; orthopedic treatment; or restoring volume effused during surgery, such as during eye surgery.
83. A method of use comprising: topically applying a composition of one or more of embodiments 1-69.
84. The method of embodiment 83, wherein the topical application is used on healthy or injured tissue in at least one of the following: cosmetology; dermatology; filling facial wrinkles; fine lines; treatment of aging skin; scarred tissue; or skin depressions.
85. A kit for administering the compositions of one or more of embodiments 1-69.

While the present disclosure has been described in connection with certain embodiments, it is to be understood that the present disclosure is not to be limited to the disclosed embodiments, but on the contrary, is intended to cover various modifications and equivalent arrangements. Also, the various embodiments described herein may be implemented in conjunction with other embodiments, e.g., aspects of one embodiment may be combined with aspects of another embodiment to realize yet other embodiments. Further, each independent feature or component of an embodiment may constitute an additional embodiment.

What is claimed is:
1. A composition, comprising at least one cross-linked protein matrix, wherein the at least one cross-linked protein matrix comprises:
  i) between 1-250 mg/mL of at least one protein residue derived from at least one amine-bearing protein;
  ii) at least one saccharide-containing cross-linking residue derived from at least one saccharide-containing cross-linking molecule comprising one or more carboxyl groups; and
  iii) at least one intermolecular cross-linkage comprising an amide bond between an amine of the at least one protein residue and a carboxyl group of the at least one saccharide-containing cross-linking molecule.
2. The composition of claim 1, wherein the composition is an injectable composition.
3. The composition of claim 1, wherein the composition is extrudable through needles of 18G to 31G to a length of between about 5 cm to about 30 cm and the extruded composition substantially holds together without surface support.
4. The composition of claim 1, wherein the composition is extrudable to a length of between 5 cm to 30 cm, 10 cm to 20 cm; or 15 cm to 30 cm without further surface support when extruded through a fine gauge needle and wherein the extruded composition is substantially coherent and substantially holds together.

5. The composition of claim 1, wherein the composition retains sufficient cohesiveness after needle extrusion such that strings of extruded composition do not break during extrusion.

6. The composition of claim 1, wherein the at least one cross-linked protein matrix comprises a 50-99.99% full length protein residue or a full length protein residue.

7. The composition of claim 1, wherein the composition enables the at least one protein residue to retain its full length, and wherein the composition is needle injectable, retains a coherent structure, and is sufficiently cross-linked to slow the composition's resorption in vivo.

8. The composition of claim 1, wherein the at least one protein residue is 50-99.99% full length or full length.

9. The composition of claim 1, wherein the composition is tissue compatible, enhances tissue in-growth, enhances tissue re-growth, or combinations thereof.

10. The composition of claim 1, wherein the at least one saccharide-containing cross-linking residue has one or more of the following properties: substantially bioavailable, substantially biodegradeable, substantially bioabsorbable, or substantially bioresorbable.

11. The composition of claim 1, wherein the at least one saccharide-containing cross-linking residue is derived from or comprises the residue of hyaluronic acid, a cellulose derivative, carboxy cellulose, carboxymethyl cellulose, hydroxymethyl cellulose, hydroxypropyl cellulose, hydroxypropyl methylcellulose, hydroxy-propylcellulose-carboxymethyl amylose, xanthan gum, guar gum, α-glucan, β-glucan, β-1,4-glucan, β-1,3-glucan, alginates, carboxymethyl dextran, a glycosaminoglycan derivative, chondroitin-6-sulfate, dermatin sulfate, heparin, heparin sulfate, polylactic acid, polyglycolic acid, poly(lactic-co-glycolic) acid, tricalcium phosphate, 1-hydroxyapatite, pharmaceutically acceptable salts of, derivatives of, or combinations thereof.

12. The composition of claim 1, wherein the at least one protein residue is derived from or comprises the residue of tropoelastin, elastin, albumin, collagen, collagen monomers, immunoglobulins, insulin, derivatives of, or combinations thereof.

13. The composition of claim 1, wherein the concentration of the at least one protein residue is in the range of between 1-200 mg/mL.

14. The composition of claim 1, wherein the at least one cross-linked protein matrix is derived from or comprises the reside of a synthetic protein substantially identical to a naturally occurring human protein.

15. The composition of claim 1, wherein the at least one cross-linked protein matrix is prepared from at least one saccharide-containing cross-linking molecule comprising at least 5% of activated carboxyl groups, modified carboxyl groups, or combinations thereof.

16. The composition of claim 1, wherein the number of protein units not incorporated into the at least one cross-linked protein matrix and left unbound is at least 1%, 3%, 5%, or 7%.

17. The composition of claim 1, wherein the at least one cross-linkage further comprises a spacer group.

18. The composition of claim 17, wherein the spacer group comprises a glycol moiety, an ethylene oxide moiety, a polyamine, a polyol, or combinations thereof.

19. The composition of claim 1, wherein the concentration of the at least one protein residue is in the range of between 5-30 mg/mL.

20. The composition of claim 1, wherein the concentration of the at least one saccharide-containing cross-linking residue is in the range of between 1-30 mg/mL.

21. The composition of claim 20, wherein the concentration of the at least one protein residue is in the range of between 25-50 mg/mL.

22. The composition of claim 21, wherein:
   i) the at least one protein residue is derived from or comprises the residue of tropoelastin; and
   ii) the at least one saccharide-containing cross-linking residue is derived from or comprises the residue of hyaluronic acid.

23. The composition of claim 8, wherein said at least one protein residue is devoid of intramolecular cross-links.

24. A method of preparing a cross-linked protein composition, comprising:
   cross-linking at least one amine-bearing protein with at least one saccharide-containing cross-linking molecule comprising one or more carboxyl groups to form at least one cross-linked protein matrix;
   wherein the at least one cross-linked matrix comprises:
   i) at least one protein residue; and
   ii) at least one saccharide-containing cross-linking residue; and
   iii) at least one intermolecular cross-linkage comprising an amide bond between the amine of the at least one amine-bearing protein and the carboxyl group of the at least one saccharide-containing cross-linking molecule.

25. The method of claim 24, wherein the prepared cross-linked protein composition is an injectable composition.

26. The method of claim 24, wherein the prepared cross-linked protein composition is extrudable through needles of 18G to 31G to a length of between 5-30 cm and the extruded composition substantially holds together without surface support.

27. The method of claim 24, wherein the prepared cross-linked protein composition retains sufficient cohesiveness after needle extrusion such that strings of extruded composition do not break during extrusion.

28. The method of claim 24, wherein the at least one protein residue is 50-99.99% full length, or full length.

29. The method of claim 28, wherein said at least one protein residue is devoid of intramolecular cross-links.

30. The method of claim 24, wherein the at least one saccharide-containing cross-linking residue has one or more of the following properties: substantially bioavailable, substantially biodegradeable, substantially bioabsorbable, or substantially bioresorbable.

31. The method of claim 24, wherein the at least one saccharide-containing cross-linking residue is derived from or comprises the residue of hyaluronic acid, a cellulose derivative, carboxy cellulose, carboxymethyl cellulose, hydroxymethyl cellulose, hydroxypropyl cellulose, hydroxypropyl methylcellulose, hydroxy-propylcellulose-carboxymethyl amylose, xanthan gum, guar gum, α-glucan, β-glucan, β-1,4-glucan, β-1,3-glucan, alginates, carboxymethyl dextran, a glycosaminoglycan derivative, chondroitin-6-sulfate, dermatin sulfate, heparin, heparin sulfate, polylactic acid, polyglycolic acid, poly(lactic-co-glycolic) acid, tricalcium phosphate, 1-hydroxyapatite, pharmaceutically acceptable salts of, derivatives of, or combinations thereof.

32. The method of claim 24, wherein the at least one protein residue is derived from or comprises the residue of tropoelastin, elastin, albumin, collagen, collagen monomers, immunoglobulins, insulin, derivatives of, or combinations thereof.

33. The method of claim 24, wherein the prepared cross-linked protein comprises a reside of a synthetic protein substantially identical to a naturally occurring human protein.

34. The method of claim 24, wherein the number of protein units not incorporated into the at least one cross-linked protein matrix and left unbound in the prepared cross-linked protein composition is at least 1%, 3%, 5%, or 7%.

35. The method of claim 24, wherein the at least one saccharide-containing cross-linking molecule comprises at least 5% of activated carboxyl groups, modified carboxyl groups, or combinations thereof.

36. The method of claim 24, wherein the prepared cross-linked protein composition comprises a concentration in the range of between 1-250 mg/mL of the at least one protein residue derived from the at least one amine-bearing protein.

37. The method of claim 24, wherein the prepared cross-linked protein composition comprises a concentration in the range of between 5-30 mg/mL of the at least one protein residue.

38. The method of claim 24, wherein the prepared cross-linked protein composition comprises a concentration in the range of between 1-30 mg/mL of the at least one saccharide-containing cross-linking residue.

39. The method of claim 38, wherein the prepared cross-linked protein composition comprises a concentration in the range of between 25-50 mg/mL of the at least one protein residue.

40. The method of claim 39, wherein:
  i) the at least one protein residue is derived from or comprises the residue of tropoelastin; and
  ii) the at least one saccharide-containing cross-linking residue is derived from or comprises the residue of hyaluronic acid.

* * * * *